US007148067B2

(12) United States Patent
Morrissey et al.

(10) Patent No.: US 7,148,067 B2
(45) Date of Patent: Dec. 12, 2006

(54) THROMBOPLASTIN REAGENTS

(75) Inventors: James H. Morrissey, Champaign, IL (US); Stephanie A. Smith, Champaign, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 0 days.

(21) Appl. No.: 10/931,282

(22) Filed: Aug. 31, 2004

(65) Prior Publication Data
US 2006/0046309 A1 Mar. 2, 2006

(51) Int. Cl.
*G01N 33/86* (2006.01)

(52) U.S. Cl. .............................. 436/69; 436/8; 436/16; 436/18; 252/408.1

(58) Field of Classification Search ................ 436/8, 436/16, 18, 63, 69, 180; 252/408.1
See application file for complete search history.

(56) References Cited

U.S. PATENT DOCUMENTS

| 3,983,004 | A |   | 9/1976  | Trobisch et al.          |
|-----------|---|---|---------|--------------------------|
| 4,139,619 | A |   | 2/1979  | Chidsey, III             |
| 4,416,812 | A | * | 11/1983 | Becker et al. ... 435/212 |
| 4,684,635 | A |   | 8/1987  | Orentreich et al.        |
| 4,784,944 | A |   | 11/1988 | Kolde                    |
| 5,059,525 | A |   | 10/1991 | Bartl et al.             |
| 5,169,786 | A |   | 12/1992 | Carroll et al.           |
| 5,192,689 | A |   | 3/1993  | Hemker et al.            |
| 5,254,350 | A |   | 10/1993 | Barrow et al.            |
| 5,270,451 | A |   | 12/1993 | Hawkins et al.           |
| 5,298,599 | A |   | 3/1994  | Rezaie et al.            |
| 5,314,695 | A | * | 5/1994  | Brown ............ 424/450 |
| 5,338,538 | A |   | 8/1994  | Tricca et al.            |
| 5,358,853 | A |   | 10/1994 | Butler et al.            |
| 5,391,380 | A |   | 2/1995  | Barrow et al.            |
| 5,418,141 | A | * | 5/1995  | Zweig et al. ...... 435/13 |
| 5,418,143 | A |   | 5/1995  | Zweig                    |
| 5,426,031 | A |   | 6/1995  | Hawkins et al.           |
| 5,504,067 | A | * | 4/1996  | Morrissey et al. ...... 514/8 |
| 5,504,193 | A |   | 4/1996  | Hawkins et al.           |
| 5,508,170 | A |   | 4/1996  | Butler et al.            |
| 5,512,304 | A |   | 4/1996  | Barrow et al.            |
| 5,580,744 | A |   | 12/1996 | Zweig                    |
| 5,599,909 | A |   | 2/1997  | Fickenscher et al.       |
| 5,625,036 | A | * | 4/1997  | Hawkins et al. ...... 430/381 |
| 5,691,380 | A |   | 11/1997 | Mason et al.             |
| 5,741,658 | A | * | 4/1998  | Morrissey ........... 435/23 |
| 5,866,425 | A | * | 2/1999  | Woodhams et al. ...... 436/16 |
| 5,888,968 | A |   | 3/1999  | Chen et al.              |
| 5,945,087 | A |   | 8/1999  | Nelson et al.            |
| 5,968,528 | A |   | 10/1999 | Deckner et al.           |
| 6,100,072 | A | * | 8/2000  | Brucato et al. ...... 435/69.7 |
| 6,194,394 | B1 |  | 2/2001  | Hawkins                  |
| 6,248,353 | B1 |  | 6/2001  | Singh                    |
| 6,261,803 | B1 |  | 7/2001  | Zander et al.            |
| 6,319,896 | B1 |  | 11/2001 | Dorin et al.             |
| 6,323,326 | B1 |  | 11/2001 | Dorin et al.             |
| 6,376,209 | B1 |  | 4/2002  | Wissel et al.            |
| 6,391,609 | B1 | * | 5/2002  | Goldford ........... 435/212 |
| 6,432,657 | B1 |  | 8/2002  | Kikuchi et al.           |
| 6,528,273 | B1 |  | 3/2003  | Hawkins                  |
| 6,706,861 | B1 |  | 3/2004  | Singh et al.             |
| 6,733,985 | B1 | * | 5/2004  | Lee ................. 435/13 |
| 6,815,424 | B1 |  | 11/2004 | Vickery et al.           |
| 2001/0004641 | A1 | | 6/2001 | Hawkins                  |
| 2002/0012699 | A1 | | 1/2002 | Singh et al.             |
| 2002/0012958 | A1 | | 1/2002 | Wissel et al.            |
| 2002/0019021 | A1 | | 2/2002 | Kraus                    |
| 2002/0132370 | A1 | | 9/2002 | Lassen et al.            |
| 2002/0151646 | A1 | | 10/2002 | Kikukawa et al.         |
| 2002/0182225 | A1 | | 12/2002 | Wang et al.              |
| 2003/0064414 | A1 | | 4/2003 | Benecky et al.           |
| 2003/0153084 | A1 | | 8/2003 | Zheng et al.             |
| 2003/0211460 | A1 | | 11/2003 | Nelsesluen              |
| 2004/0037893 | A1 | | 2/2004 | Hansen et al.            |
| 2004/0043933 | A1 | | 3/2004 | Hansen et al.            |
| 2004/0084867 | A1 | | 5/2004 | Leyland-Jones            |
| 2004/0086953 | A1 | * | 5/2004 | Jenny et al. ....... 435/13 |

FOREIGN PATENT DOCUMENTS

| EP | 0 727 434    | 8/1996  |
|----|--------------|---------|
| EP | 0 942 284    | 9/1999  |
| WO | WO 93/07492  | 4/1993  |
| WO | WO 98/44352  | 10/1998 |
| WO | WO 00/62742  | 10/2000 |

OTHER PUBLICATIONS

Bader R, Mannucci PM, Tripodi A, Hirsh J, Keller F, Solleder EM, Hawkins P, Peng M, Pelzer H, Teijidor LM, et al. Multicentric evaluation of a new PT reagent based on recombinant human tissue factor and synthetic phospholipids. Thromb Haemost 1994; 71:292-299.

Hirsh J, Fuster V, Ansell J, Halperin JL. American Heart Association/American College of Cardiology Foundation guide to warfarin therapy. Circulation 2003: 107: 1692-1711.

Hoots, K., Disseminated Intravacular Coagulation (DIC) Minutes from Jun. 18, 2004 meeting, pp. 1-6.

Jackson C. Monitoring Oral Anticoagulant Therapy—INR values for the Owren Prothrombin Time, Hemosaga Diagnostics Corporation, San Dieto, CA, Dec. 5, 2003, Thromb Haemost 2004; 91: 210-212.

Kemball-Cook G, Gamer I, Imanaka Y, Nishimura T, O'Brien DP, Tuddenham EG, McVey JH. High-level production of human blood coagulation factors VII and XI using a new mammalian expression vector. Gene. Feb. 25, 1994;139(2):275-279.

(Continued)

Primary Examiner—Maureen M. Wallenhorst
(74) Attorney, Agent, or Firm—Evan Law Group LLC

(57) ABSTRACT

A thromboplastin reagent includes tissue factor, Factor VIIa, and a net negatively charged phospholipid. The thromboplastin reagent is a synthetic thromboplastin reagent, and is in dried form.

64 Claims, 9 Drawing Sheets

OTHER PUBLICATIONS

Kitchen S, Jennings I, Woods TA, Walker ID, Preston FE. Two recombinant tissue factor reagents compared to conventional thromboplastins for determination of international normalised ratio: a thirty-three-laboratory collaborative study. The Steering Committee of the UK National External Quality Assessment Scheme for Blood Coagulation. Thromb Haemost 1996: 76:372-376.

Kitchen S, Preston FE. Standardization of prothrombin time for laboratory control of oral anticoagulant therapy. Semin Thromb Hemost 1999; 25:17-25.

Massignon D, Moulsma M, Bondon P, Debize G, Abidi H, Buttin T, Bon C, Pilllonchery G, Coeur P. Prothrombin time sensitivity and specificity to mild clotting factor deficiencies of the extrinsis pathway: evaluation of eight commercial thromboplastins. Thromb Haemost 1996; 75:590-594.

Morrison M., Caldwell A., McQuacker G., Fitzsimons EJ., Discrepant INR values: a comparison between Manchester and Thrombotest reagents using capillary and venous samples. Clin Lab Haematol 1989; 11(4):393-398.

Morrissey JH, Fakhrai H, Edgington TS. Molecular cloning of the cDNA for tissue factor, the cellular receptor for the initiation of the coagulation protease cascade. Cell 1987; 50:129-135.

Morrissey JH. Tissue factor: an enzyme cofactor and a true receptor. Thromb Haemost 2001; 86:66-74.

Neuenschwander PF, Bianco-Fisher E, Rezale AR, Morrissey JH. Phosphatidylethanolamine augments factor Villa-tissue factor activity: enhancement of sensitivity to phosphatidylserine. Biochemistry 1995; 34:13988-13993.

Poller L, Barrowcliffe TW, Van Den Besselaar AM, Jespersen J, Tripodi A, Houghton D. Minimum lyophilized plasma requirement for ISI calibration. European Concerted Action on Anticoagulation. Am J Clin Pathol 1998; 109:196-204.

Poller L. International Normalized Ratios (INR): the first 20 years. J. Thromb Haemost. Jun. 2004;2(6):849-60.

Rezaie AR, Fiore MM, Neuenschwander PF, Esmon CT, Morrissey JH. Expression and purificationof a soluble tissue factor fusion protein with an epitope for an unusual calcium-dependent antibody. Protein Expr Purif 1992; 3:453-460.

Roussi J, Drouet L, Samama M, Sie P. French multicentric evaluationof recombinant tissue factor (recombiplastin) for determination of prothrombin time. Thromb Haemost 1994; 72:698-704.

Search for USPTO website dated May 26, 2004, for key words "Factor VII" AND thromboplastin.

Search from USPTO website dated May 27, 2004, for key words "Factor VII" AND thromboplastin, PGPUB Production Database.

Smith SA, Morrissey JH. Rapid and efficient incorporation of tissue factor into liposomes, J Thromb Haemost 2004; 2:1155-1162. (provided as a preprint of the paper).

Testa S, Morstabilini G, Fattorini A, Galli L, Denti N, D'Angelo A. Discrepant sensitivity of thromboplastin reagents to clotting factor levels explored by the prothrombin time in patients on stable oral anticoagulant treatment: impact on the international normalized ration system. Haematologica 2002; 87:1265-1273.

Van Den Besselaar AM, Tripodi A, Poller L. WHO guidelines for thromboplastins and plasma used to control oral anticoagulation therapy. Annex 3. World Health Organ Tech Rep Ser 1999; 889: 64-93.

Watson C, Kitchen S, Woolley AM, Young L, Malia RG. Recombinant and tissue extract thromboplastins for determination of international normalised ration in over-anticoagulated patients. Br J Biomed Sci 1999; 56:123-127.

Zwaal RF. Membrane and lipid involvement in blood coagulation. Biochim Biophys Acta 1978; 515:163-205.

Abstract of: Smith, S.A., et al., "Do elevated plasma tissue factor pathway inhibitor (TFPI) levels affect measurement of factor Vlla?"., Blood, vol. 104, issue 11, (2004).

Abstract of: Smith, S.A., et al., "Polyphosphates—A novel modulator of coagulation"., Artheriosclerosis, Thrombosis, and Vascular Biology, Journal of the American Heart Association, Abstracts of the 6th Annual Conference on arteriosclerosis, Thrombosis and Vascular Biology, vol. 25, 4 pages, (2005).

Bouma, B.N., et al., Thrombin-activatable fibrinolysis inhibitor (TAFI, plasma procarboxypeptidase B, procarboxypeptidase R, procarboxypeptidase U(., Journal of Thrombosis and Haemostasis, vol. 1, pp. 1566-1574, (2003).

Bajzar, L., et al., "Thrombin activatable fibrinolysis inhibitor: not just an inhibitor of fibrinolysis"., Crit. Care Med., vol. 32, pp. S320-S324, (2004).

Banner, D.W., et al., "The crystal structure of the complex of blood coagulation factor Vlla with soluble tissue factor"., Nature, vol. 380, pp. 41-46, (1996).

Boffa, M. B., et al., "Roles of thermal instability and proteolytic cleavage in regulation of activated thrombin-activable fibrinolysis inhibitor"., J Biol. Vhem., vol. 275, pp. 12868-12878, (2000).

Broze, G. J., Jr. "Tissue factor pathway inhibitor"., Thromb. Haemost., vol. 74, pp. 90-93, (1995).

Camerer, E., et al., "Notes on the cell biology of tissue factor"., Haemostasis, vol. 26, pp. 25-30, (1996).

Chikh, G.G., et al., "Attaching histidine-tagged peptides and proteins to lipid-based carriers through use of metal-ion-chelating lipids"., "Tethered-bilaver lipid membranes as a support for membrane-active peptides"., Biochem. Soc. Trans., vol. 29, pp. 613-617, (2001).

Cornell, B.A., et al., "Tethered-bilayer lipid membranes as a support for membrane-active peptides"., Biochem. Soc. Trans., vol. 29, pp. 613-617, (2001).

Dano, K., et al., "Plasminogen activators, tissue degradation, and cancer"., Adv. Cancer Res., vol. 44, pp. 139-266, (1985).

Darst, S.A., "A new twist on protein crystallization"., Proc. Natl. Acad. Sci. USA, vol. 95, pp. 7848-7849, (1998).

Docampo, R., et al., "Acidocalcisomes—conserved from bacteria to man"., Nature Rev. Microbiol., vol. 3, pp. 251-261, (2005).

Fiore, M.M., et al., "The biochemical basis for the apparent defect of soluble mutant tissue factor in enhancing the proteolytic activities of factor Vlla"., J. Biol. Chem., vol. 269, pp. 143-149, (1994).

Fiore, M.M., et al., "An unusual antibody that blocks tissue factor/ factor Vlla function by inhibiting cleavage only of macromolecular substrates"., Blood, vol. 80, pp. 3127-3134, (1992).

Gemmell, C.H., et al., "Flow as a regulator of the activation of factor X by tissue factor"., Blood, vol. 72, pp. 1404-1406, (1988).

Gemmell, C.H., et al., "The effects of shear rate on the enzymatic activity of the tissue factor-factor Vlla complex"., Microvasc. Res., vol. 40, pp. 327-340, (1990).

Gemmell, C.H., et al., "Utilizatiion of a continuous flow reactor to study the lipoprotein-associated coagulation inhibitor (LACI) that inhibits tissue factor"., Blood, vol. 76, pp. 2266-2271, (1990).

Groves, J.T., et al., "Supported planar bilayers in studies on immune cell adhesion and comunication"., J. Immunol. Methods, vol. 278, pp. 19-32, (2003).

Jeong, S.W., et al., "Synthesis of a polymerizable metal-ion-chelating lipid for fluid bilayers"., J. Org. Chem., vol. 66, No. 14, pp. 4799-4802, (2001).

Jones, D.T., "Do transmembrane protein superfolds exist?", FEBS Letters, vol. 423, pp. 281-285, (1998).

Kubalek, E.W., et al., "Two-dimensional crystallization of histidine-tagged, HIV-1 reverse transcriptase promoted by a novel nickel-chelating lipid"., J. Structural Biology, vol. 113, pp. 117-123, (1994).

Lauer, S.A., et al., "Development and characterization of Ni-NTA-bearing microspheres"., Cytometry, vol. 48, pp. 136-145, (2002).

Lazarus, R.A., et al., "Inhibitors of Tissue Factor*Factor Vlla for anticoagulant therapy"., Curr. Med. Chem., vol. 11, pp. 2275-2290, (2004).

Linkins, L.A., et al., "New anticoagulant therapy"., Annu. Rev. Med., vol. 56, pp. 63-77, (2005).

Lorenz, B., et al., "Mammalian intestinal alkaline phosphatase acts as highly active exopolyphosphatase"., Biochim. Biophys. Acta, vol. 1547, pp. 254-261, (2001).

Lorenz, B., et al., "Anti-HIV-1 activity of inorganic polyphosphates"., J. Acquir. Immune. Defic. Syndr. Hum. Retrovirol., vol. 14, pp. 110-118, (1997).

Marx, P.F., et al., "Inactivation of active thrombin-activable fibrinolysis inhibitor takes place by a process that involves conformational instability rather than proteolytic cleavage"., J. Biol. Chem., vol. 275, pp. 12410-12415, (2000).

Marx, P.F., et al., "Plasmin-mediated activation and inactivation of thrombin-activatable fibrinolysis inhibitor"., Biochemistry, vol. 41, pp. 6688-6696, (2002).

Morrissey, J.H., "Tissue factor and factor VII initiation of coagulation". In: Colman RW, Hirsh J, Marder VJ, Clowes AW, George JN, editors, Hemostasis and Thrombosis: Basic Principles and Clinical Practice Philadelphia, Lippincott Williams & Wilkins. pp. 89-101, (2001).

Morrissey, J.H., et al., "Quantitation of activated factor VII levels in plasma using a tissue factor mutant selectively deficient in promoting factor VII activation"., Blood, vol. 81, pp. 734-744, (1993).

Morrissey, J.H., et al., "Factor VIIa-tissue factor: functional importance of protein-membrane interactions"., Thromb. Haemost., vol. 78, pp. 112-116, (1997).

Morrissey, J.H., et al., "Monoclonal antibody analysis of purified and cell-associated tissue factor"., Thromb. Research, vol. 52, pp. 247-261, (1988).

Mosnier, L.O., et al., "Identification of thrombin activatable fibrinolysis inhibitor (TAFI) in human platelets"., Blood, vol. 101, pp. 4844-4846, (2003).

Nakagaki, T., et al., "Initiation of the extrinsic pathway of blood coagulation: evidence for the tissue factor dependent autoactivation of human coagulation factor VII"., Biochemistry, vol. 30, pp. 10819-10824, (1991).

Nemerson, Y., et al., "Tissue factor accelerates the activation of coagulation factor VII: The role of a bifunctional coagulation cofactor"., Thromb. Res., vol. 40, pp. 3551-358, (1985).

Nesheim, M., et al., "Thrombin, thrombomodulin and TAFI in the molecular link between coagulation and fibrinolysis"., Thromb. Haemost, vol. 78, pp. 386-391, (1997).

Neuenschwander, P.F., et al., "Roles of the membrane-interactive regions of factor VIIa and tissue factor. The factor VIIa Gla domain is dispensable for binding to tissue factor but important for activation of factor X"., J. Biol. Chem., vol. 269, pp. 8007-8013, (1994).

Neuenschwander, P.F., et al., "Deletion of the membrane anchoring region of tissue factor abolishes autoactivation of factor VII but not cofactor function. Analysis of a mutant with a selective deficiency in activity"., J. Biol. Chem., vol. 267, pp. 14477-14482, (1992).

Neuenschwander, P.F., et al., "Factor VII autoactivation proceeds via interaction of distinct protease-cofactor and zymogen-cofactor complexes, Implications of a two-dimensional enzyme kinetic mechanism"., J. Biol. Chem., vol. 268, pp. 21489-21492, (1993).

Nilsson, J., et al., "Comparative analysis of amino acid distributions in integral membrane proteins from 107 genomes"., Proteins, vol. 60, pp. 606-616, (2005).

Novotny, W.F., et al., "Platelets secrete a coagulation inhibitor functionally and antigenically similar to the lipoprotein associated coagulation inhibitor"., Blood, vol. 72, pp. 2020-2025, (1988).

Paborsky, L.R., et al., "Lipid association, but not the transmembrane domain, is required for tissue factor activity. Substitution of the transmembrane domain with a phosphatidylinositol anchor"., J. Biol. Chem., vol. 266, pp. 21911-21916, (1991).

Repke, D., et al., "Hemophilia as a defect of the tissue factor pathway of blood coagulation: effect of factors VIII and IX on factor X activation in a continuous-flow reactor"., Proc. natl. Acad. Sci. USA, vol. 87, pp. 7623-7627, (1990).

Rojkjaer, R., et al., "Activatin of the plasma kallikrein/kinin system on endothelial cell membranes"., Immunopharmacology, vol. 43, pp. 109-114, (1999).

Ruf, W., et al., "Phospholipid-independent and -dependent interactions requied for tissue factor receptor and cofactor function"., J. Biol. Chem., vol. 266, pp. 2158-2166, (1991).

Sandset, P. M., et al., "Heparin induces release of extrinsic coagulation pathway inhibitor (EPI)"., Thromb. Res., vol. 50, pp. 803-813, (1988).

Schneider, M., et al., "Two naturally occurring variants of TAFI (Thr-325 and Ile-325) differ substantially with respect to thermal stability and antifibrinolytic activity of the enzyme"., J. Biol. Chem., vol. 277, pp. 1021-1030, (2002)

Seddon, A.M., et al., "Membrane proteins, lipids and detergents: not just a soap opera"., Biochim. biophys. Acta., vol. 1666, pp. 105-117, (2004).

Shigematsu, Y., et al., "Expressiion of human soluble tissue factor in yeast and enzymatic properties of its complex with factor VIIa"., J. Biol. chem., vol. 267, pp. 267, pp. 21329-21337, (1992).

Smith, S.A., et al., "Properties of recombinant human thromboplastin that determine the International Sensitivity Index (ISI)"., J. Thromb. Haemost., vol. 2, pp. 1610-1616, (2004).

Terpe, K., "Overview of tag protein fusions: from molecular and biochemical fundamentals to commercial systems"., Appl. Microbiol. Biotechnol., vol. 60, pp. 523-533, (2003).

Tripodi, A., et al., "Recombinant tissue factor as substitute for conventional thromboplastin in the prothrombin time test"., Thromb. Haemost, vol. 67, pp. 42-45, (1992).

Wallin, E., et al., "Genome-wide analysis of integral membrane proteins from eubacterial, archaean, and eukaryotic organisms"., Protein Sci., vol. 7, pp. 1029-1038, (1998).

Waxman, E., et al., "Human factor VIIa and its complex with soluble tissue factor: Evaluation of asymmetry and conformational dynamics by ultracentrifugation and fluorescence anisotropy decay methods"., Biochemistry, vol. 32, pp. 3005-3012, (1993).

Waxman, E., et al., "Tissue factor and its extracellular soluble domain: The relationship between intermolecular association with factor VIIa and enzymatic activity of the complex"., Biochemistry, vol. 31, pp. 3998-4003, (1992).

Bajzar, L., et al., "TAFI, or plasma procarboxypeptidase B, couples the coagulation and fibrinolytic cascades through the thrombin-thrombomudulin complex"., Journal of Biological Chemistry, vol. 271, No. 28, pp. 16603-16608, (1996).

Barrowcliffe, T.W., et al.,"Studies of phospholipid reagents used in coagulation I: Some general properties and their sensitivity to factor VIII"., Thrombosis and Haemostasis, Stuttgart, DE, vol. 46, No. 3, pp. 629-633, (1981).

Bladbjerg, E. M., et al., "In vitro effects of heparin and tissue factor pathway inhibitor on factor VIII assays. Possible implications for measurements in vivo after heparin therapy"., Blood Coagulation and Fibrinolysis, vol. 11, No. 8, pp. 739-745. (2000).

Hansen, J.-B., et al., "Reduction of factor FVCIIa activity during heparin therapy evidence for assay interactions with tissue factor pathway inhibitor and antithrombin"., Thromb. Res., vol. 100, pp. 389-396, (2000).

International Search Report dated Mar. 1, 2006 for corresponding PCT application No. PCT/US2005/029873.

Kent, M.S., et al., "Segment concentration profile of myoglobin adsorbed to metal ion chelating lipid monolayers at the air-water interface by neutron reflection"., Langmuir, vol. 18, No. 9, pp. 3754-3757, (2002).

Kornberg, A. "Inorganic polyphosphate: Toward making a forgotten polymer unforgettable"., Journal of Bacteriology, vol. 177, No. 3, pp. 491-496, (1995).

Nesheim, M., "Thrombin and fibrinolysis"., Chest, vol. 124, No. 3, pp. 33S-39S, (2003).

Ruiz, F.A., et al., "Human platelet dense granules contain polyphosphate and are similar to acidocalcisomes of bacteria and unicellular eukaryotes"., Journal of Biological Chemistry, vol. 279, No. 43, pp. 44250-44257, (2004).

Smith, S. A., et al., "Rapid and efficient incorporation of tissue factor into liposomes"., J. Thromb. Haemost., vol. 2, pp. 1155-1162, (2004).

Smith, A., et al., "Properties of recombinant human thromboplastin that determine sensitivity to vitamin K-dependent coagulation factors"., Blood, vol. 104, No. 11, part 1, pp. 155A, 46th Annual meeting of the American Society of Hematology, San Diego, CA, USA, Dec. 4-7, 2004.

Waters, E.K., et al., "Restoring full biological activity to the isolated ectodomain of an integral membrane protein"., Biochemistry, vol. 45, No. 11, pp. 3769-3774, (2006).

Jackson, C.M., "Monitoring oral anticoagulant therapy-INR values for the Owren prothrombin time"., Thromb Haemost, vol. 91, pp. 210-212, (2004).

Stone, M.J., et al., "Recombinant soluble human tissue factor secreted by *Saccharomyces cerevisiae* and refolded for *Escherichia coli* inclusion bodies: glycosylation of mutants, activity and physical characterization"., J. Biochem., vol. 310, pp. 605-614, (1995).

\* cited by examiner

THROMBOPLASTIN REAGENTS

FEDERALLY SPONSORED RESEARCH OR DEVELOPMENT

The subject matter of this application may in part have been funded by NIH (NHLBI) SCOR grant P50 HL45402. The government may have certain rights in this invention.

BACKGROUND

The Prothrombin Time (PT) test is widely used to monitor oral anticoagulation therapy by coumarins, as a general screening test for the blood clotting system, and as the basis for specific Factor assays. Clotting times obtained with the PT are primarily dependent on the plasma levels of the vitamin K-dependent coagulation Factors II (prothrombin), VII, and X, and on the levels of two non-vitamin K-dependent proteins, Factor V and fibrinogen. Coumarin treatment antagonizes the vitamin K carboxylase/reductase cycle, thus inhibiting the post-translational conversion of glutamate residues to gamma-carboxyglutamate. Vitamin K-dependent clotting factors contain essential gamma-carboxyglutamate residues in their Gla domains. Patients receiving coumarin therapy will therefore produce undercarboxylated vitamin K-dependent clotting factors with reduced procoagulant activity. This prolongs the PT, chiefly due to depression in the levels of Factors II, VII and X. Successful oral anticoagulant therapy with coumarins requires careful monitoring of the patient's PT in order to achieve an effective level of anticoagulation while minimizing bleeding complications (reviewed by Hirsh et al. [1]).

The PT test is accomplished by mixing citrated plasma samples with a thromboplastin reagent and measuring the time to clot formation. An active ingredient in thromboplastin reagents is tissue factor, the protein responsible for triggering the blood clotting cascade through the extrinsic pathway [2]. Originally, thromboplastin reagents were prepared from relatively crude extracts of tissues (usually brain or placenta) of human or animal origin. More recently, however, newer generation thromboplastin reagents have been developed that are based on purified, recombinant human tissue factor that has been reconstituted into phospholipid vesicles [3,4]. Because thromboplastin reagents vary widely in composition and manner of preparation, their sensitivities in monitoring oral anticoagulant therapy also vary widely. More sensitive thromboplastin reagents exhibit a more marked prolongation in the patient's PT as a consequence of oral anticoagulant therapy than do less sensitive thromboplastin reagents. Left uncorrected, this can result in markedly different dosing of oral anticoagulants [1].

Several years ago, a system was introduced to correct for differences in the sensitivities of thromboplastin reagents to coumarin therapy. Termed the International Sensitivity Index (ISI), this scheme has gained wide acceptance for measuring the responsiveness of a particular thromboplastin reagent to the decrease in coagulation proteins induced by administration of coumarin drugs [1]. The process for assigning an ISI value to a given lot of thromboplastin reagent is begun by measuring the clotting times of a collection of plasma samples consisting of a relatively large group of normal donors and patients who are stably anticoagulated with coumarins [5]. The clotting times of these same plasmas are also measured using an international reference thromboplastin of known ISI value. The ISI value of the new thromboplastin reagent is then derived from the slope of the regression line fitted to the clotting times obtained with the two reagents, plotted on log-log graphs. These ISI values are ultimately traceable to an original international thromboplastin standard, which was assigned an ISI value of 1.00 [5]. The more sensitive a thromboplastin reagent is to the changes induced by coumarin therapy, the lower its ISI value. In general, thromboplastin reagents with ISI values near 1.0 have been the most desirable. Indeed, newer generation reagents (including those based on recombinant thromboplastin) have typically been manufactured to have ISI values near 1.0 [1].

The ISI value of a thromboplastin reagent is used to calculate the International Normalized Ratio (INR) for patient plasma samples. The INR is calculated by first dividing the patient's PT value by the mean PT value for 20 or more normal plasmas. This PT ratio is then raised to the ISI power, yielding the INR value, which in turn, is used by the treating physician to adjust the drug dose. The introduction of the INR reporting system has vastly improved the standardization of monitoring of oral anticoagulant therapy, and can be credited with decreasing bleeding complications for oral anticoagulant therapy [1].

Although the ISI/INR scheme has revolutionized the way in which oral anticoagulant therapy is monitored, it has been criticized on a number of grounds. For example, experience with this system has demonstrated that a single ISI value for each new lot of thromboplastin reagent is not sufficient. Instead, ISI values are determined for each combination of thromboplastin lot and the type of coagulometer used to measure clotting times [6]. For careful monitoring of patient INR values, some have recommended that clinical coagulation laboratories perform local calibrations using plasma calibrants for particular combinations of thromboplastin reagent and instrumentation used to measure patient PT values [6]. In addition, the determination of ISI depends upon a linear relationship (on log-log plots) between clotting times determined with the test and reference thromboplastin reagents, but a number of instances of deviation from linearity have been reported, especially for patients with high INR values [7–9]. Recombinant thromboplastin reagents have also been criticized as being overly sensitive to changes in Factor VII levels, relative to tissue-derived thromboplastin reagents [8, 10].

BRIEF SUMMARY

In a first aspect, the present invention is a thromboplastin reagent, comprising (a) TF, (b) FVII, and (c) a net negatively charged phospholipid. The thromboplastin reagent is a synthetic thromboplastin reagent, and is in dried form.

In a second aspect, the present invention is a thromboplastin reagent, comprising (a) TF, (b) FVII, and (c) a net negatively charged phospholipid. The thromboplastin reagent is a synthetic thromboplastin reagent, and does not comprise Factor II or Factor X.

In a third aspect, the present invention is a thromboplastin reagent, comprising (a) TF, (b) 1–1000 pM Factor VIIa equivalents of FVII, and (c) a net negatively charged phospholipid. The thromboplastin reagent is a synthetic thromboplastin reagent.

In a fourth aspect, the present invention is a thromboplastin reagent, comprising (a) rTF, (b) at least 150 pM Factor VIIa, (c) PC, (d) PS, and (e) $Ca^{2+}$. The thromboplastin reagent has an ISI of at most 1.5, a PTR for 1% Factor VII of at most 1.5, and a PTR for 1% Factor II of at least 2.

In a fifth aspect, the present invention is a method of making a thromboplastin reagent, comprising adding FVII to a synthetic thromboplastin reagent; and drying the thromboplastin reagent.

In a sixth aspect, the present invention is a method of changing the ISI of a thromboplastin reagent, comprising adding FVII to a thromboplastin reagent.

Definitions

Factor-seven (FVII) means any protein that exhibits Factor VII clotting activity of human Factor VII. The Factor VII clotting activity of a protein is determined by comparing the amount of the protein necessary to give the same clotting time as human Factor VII in the following assay: 50 µL of citrated Factor VII deficient plasma, together with human Factor VII or the protein, is incubated in a cuvette for 2 min at 37$20$ C., after which clotting is initiated by adding 100 µL pre-warmed thromboplastin reagent, and the time to clot formation is measured with a coagulometer, such as an ST4 coagulometer (Diagnostica Stago, Parsippany, N.J.). The amount of human Factor VII and the type of thromboplastin reagent are preferably selected to give a clotting time of 10–15 seconds. The molar amount of human Factor VII that achieves a given clotting time is divided by the molar amount of the protein that gives the same clotting time, which gives the relative Factor VII clotting activity of the protein. Preferably, FVII has at least 1% of the clotting activity of human Factor VII. FVII includes, for example, natural human Factor VII, natural human Factor VIIa, recombinant human Factor VII [17] and VIIa, and other mammalian Factor VII and VIIa (such as natural rabbit Factor VII and natural rabbit Factor VIIa).

"Factor VIIa equivalents" means that the amount of FVII present has the same clotting activity as the specified amount of natural human Factor VIIa. For example, "10 ng Factor VIIa equivalents of FVII" means that the amount of FVII present has the same clotting activity as 10 ng of natural human Factor VIIa.

r-tissue-factor (rTF) means any recombinant tissue factor which is not identical to natural mammalian tissue factor. This includes recombinant tissue factor produced in bacteria (which differs from natural mammalian tissue factor in molecular weight since it does not have attached carbohydrate), and recombinant tissue factor produced in insect cells (baculovirus) (which differs from natural mammalian tissue factor in molecular weight, since certain problematic domains have been removed).

Tissue-factor (TF) means any tissue factor protein, such as rTF and natural mammalian tissue factors.

Thromboplastin reagent is any reagent which contains TF and that when 100 µL of the reagent pre-warmed to 37° C. is mixed with 50 µL plasma pooled from normal individuals will result in clotting within 1 minute; and when neat and warmed to 37° C. does not clot within 2 minutes.

Synthetic thromboplastin reagent is any thromboplastin reagent that contains rTF. Alternatively, synthetic thromboplastin reagent contains TF and does not contain any actin, hexokinase, and alkaline phosphatase.

"Prothrombin time ratio" (PTR) for a "1% Factor" of a thromboplastin reagent is determined by dividing the PT for a plasma containing 1% of the normal level of the specified factor by the PT for pooled normal plasma (100% factor) obtained with the thromboplastin reagent. For example, the "prothrombin time ratio for 1% Factor VII" of a thromboplastin reagent is determined by dividing the PT for a plasma containing 1% of the normal level of Factor VII by the PT for pooled normal plasma (100% factor) obtained with the thromboplastin reagent.

DETAILED DESCRIPTION

Figure 1:
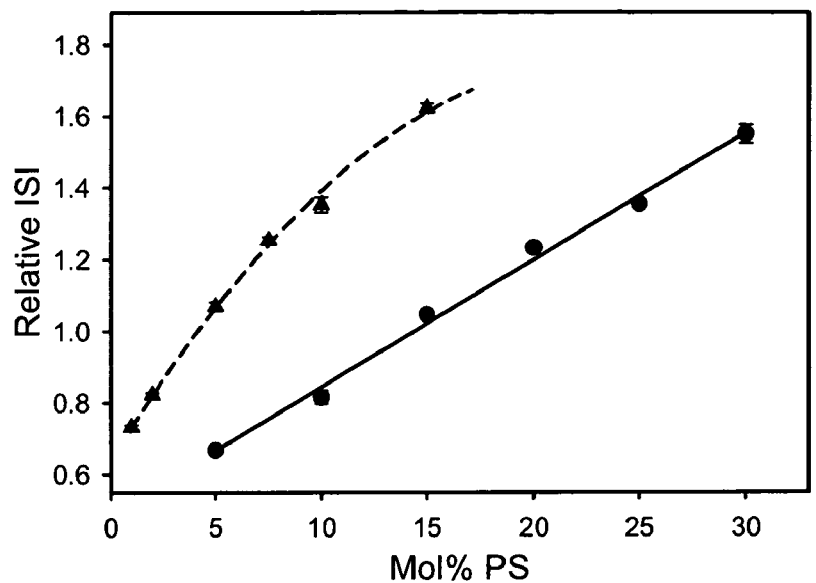
FIG. 1 is a graph of the relationship between thromboplastin sensitivity as measured by ISI and phospholipid composition.

We hypothesized that a major difference between thromboplastin reagents made from tissue extracts and thromboplastin reagents made using recombinant human tissue factor is that the tissue-derived thromboplastins may be contaminated with Factor VII (the plasma protein that serves as the ligand for tissue factor), while recombinant reagents would be devoid of Factor VII. We felt that this is likely to explain why recombinant reagents are so much more sensitive to changes in plasma Factor VII levels than are tissue-derived reagents. We found that adding small amounts of Factor VIIa to thromboplastin reagents made from purified ingredients (recombinant human tissue factor and purified phospholipids) greatly decreased their sensitivity to changes in Factor VII levels in plasma. Very surprising, however, was that adding even tiny amounts of Factor VIIa to such thromboplastin reagents dramatically altered their sensitivities to other clotting factors as well (chiefly, Factor X and prothrombin). Furthermore, we found strongly synergistic interactions between added Factor VIIa and changes in the levels of negatively charged phospholipids and changes in the ionic strength of recombinant thromboplastins. This was reflected in surprisingly profound changes in the sensitivities of such reagents to Factor VII, Factor X and prothrombin. Taken together, these alterations to the formulation of thromboplastin reagents has given us almost complete control over the sensitivities of such reagents to Factor VII, Factor X, and prothrombin, and to a very large extent, these sensitivities can be individually manipulated.

Regression models have been developed describing the relationship of ISI to reagent composition that allow for design of reagents of any desired specific level of response. Specifically, reagents containing low amounts of negatively charged phospholipid (such as phosphatidylserine) and/or high NaCl content are more responsive to the clotting factor deficits induced by oral anticoagulation (as measured by ISI). Additionally, further experiments have elucidated the relationships between reagent response to individual coagulation factors and the composition of the reagent. Response to prothrombin (Factor II) is particularly sensitive to changes in phosphatidylserine and salt content. Since a number of studies suggest that the levels of this factor are most directly associated with risk for thrombosis, increasing the sensitivity of the thromboplastin reagent to changes in Factor II has the potential to improve the efficacy and safety of oral anticoagulant therapy. Addition of minute amounts of Factor VIIa to the thromboplastin reagent can be used to minimize sensitivity to Factor VII and to further manipulate responses to other factors. Since Factor VII has the shortest biological half-life, and the least impact on risk for thrombosis, eliminating a reagent's response to this factor may also significantly improve reagent performance. Reagents of any specific desired factor sensitivity can now be designed. Specific reagents will be produced for simplified clotting tests that respond primarily to deficiencies of the coagulation factors of interest in the particular disease process.

Thromboplastin reagents of the present invention contain added FVII. Any FVII may be used including any mammalian Factor VII or VIIa (such as human, rabbit, rat, cow, etc.). Preferably the thromboplastin reagents contain added Factor VIIa, more preferably human Factor VIIa. The FVII may be prepared recombinantly [17].

Preferably, the amount of FVII present is less than the amount of Factor VII or Factor VIIa found in the plasma of normal individuals, including the amount of Factor VII or VIIa found in Factor II- and Factor X-deficient plasmas. The amount of FVII present is preferably 0.1 to 10 nanograms/milliliter (ng/ml) Factor VIIa equivalents, 1 to 6 ng/ml Factor VIIa equivalents, or 2.5 to 5 ng/ml Factor VIIa equivalents, and more preferably at least 1 ng/ml or at least 2.5 ng/ml Factor VIIa equivalents. Alternatively, the amount of FVII may be expressed in picomolar (pM) amounts; such as 1–1000 pM Factor VIIa equivalents, 50–400 pM Factor VIIa equivalents, preferably at least 150 pM Factor VIIa equivalents or at least 200 pM Factor VIIa equivalents.

Preferably, the thromboplastin reagent contains $Ca^{2+}$, or the $Ca^{2+}$ may be added just prior to use of the reagent. The $Ca^{2+}$ may be provided with the thromboplastin reagent in a kit, with each part separately packed, optional with each reagent is dry form. $Ca^{2+}$ is preferably added as $CaCl_2$. The amount of $Ca^{2+}$ is preferably 1–100 mM, more preferably 5–75 mM, more preferably 15–50 mM, including 20 mM, 25 mM, 30 mM, 35 mM, 40 mM and 45 mM.

Ionic strength may be adjusted by adding salts, such as alkali metal and alkaline earth metal salts, including halides, sulfates, nitrates and acetates, such as NaCl and KCl. Preferably, the salts are present in an amount of 0–200 mM, 10–150 mM, 15–125 mM, or more preferably 25–100 mM.

Preferably, the thromboplastin reagent does not contain one or more of Factor II, Factor X, actin, hexokinase, and alkaline phosphatase. The absence of actin, hexokinase and alkaline phosphatase indicates that the thromboplastin reagent does not contain tissue extracts (although the tissue factor itself may have been isolated and purified from tissue). The absence of Factor II and Factor X indicates that neither Factor II nor Factor X deficient plasmas have been added to the reagent.

The thromboplastin reagents contain TF relipidated into phospholipids, such as phosphatidylcholine (PC), phosphatidylserine (PS) and phosphatidylethanolamine (PE). At least a portion of the phospholipids are net negatively charged phospholipids, such as PS, phosphotidylglycerol (PG), phosphatidic acid (PA), and phosphotidylinositol (PI). Preferably, the amount of PS is from 5–50%, more preferably from 10–40%, including 15%, 20%, 25%, 30%, and 35%, of the total phospholipids content. The amount of PE is preferably 0–50%, more preferably 5–40%, including 10%, 15%, 20%, 25%, 30%, and 35%, of the total phospholipids content. Preferably, the remainder of the phospholipids content is composed of neutral phospholipids, such as PC, for example 0–95%, more preferably 40–90%, including 45%, 50%, 55%, 60%, 65%, 70%, 75%, 80%, and 85%, of the total phospholipid content.

The ISI of the thromboplastin reagent is preferably 0.6 to 2, more preferably 0.8 to 1.5, even more preferably 0.8 to 1.2, and most preferably 0.9 to 1.1. Alternatively, preferably the ISI of the thromboplastin reagent is at most 1.5 or at most 1.2.

Preferably, the PTR for 1% Factor VII is 1–10, more preferably 1–5, even more preferably 1–2, and most preferably at most 1.5, including at most 1.4, 1.3, 1.2 and 1.1.

Preferably, the PTR for 1% Factor II (prothrombin) is 1–10, more preferably 1.5–7, even more preferably 2–7, and most preferably at least 2, including at least 3, 4, 5 and 6.

Preferably, the PTR for 1% Factor X is 1–10, including 1.1, 1.2, 1.3, 1.4, 1.5, 1.6, 1.7, 1.8, 1.9, 2, 3, 4, 5, 6 and 7.

Preferably, the PTR for 1% Factor VII is at most 2 and the PTR for 1% Factor II is at least 4; more preferably the PTR for 1% Factor VII is at most 1.5 and the PTR for 1% Factor II is at least 5; and most preferably the PTR for 1% Factor VII is at most 1.2 and the PTR for 1% Factor II is at least 6.

The thromboplastin reagents may be provided in dried form, by freeze-drying, spray-drying, or other suitable protein drying methods. The reagents may be dried onto strips or other solid supports, and may be provided as kits with the components provided separately packaged, or groups of the components packaged into 2 or more packages. Some or all of the components may be provided in dried forms, and other components provided in saline or a physiological buffer.

Thromboplastin reagents may be used to monitor any anticoagulant drug therapy. Table 1 below lists a variety of these drugs.

TABLE 1

Anticoagulant drugs that may be monitored with thromboplastin reagents

| | |
|---|---|
| Coumarin Derivatives (block production of functional factors II, VII, and X): | Warfarin (COUMADIN ®)[1]<br>Nicoumalone (ACENOCOUMAROL ™)[1]<br>Dicoumarol (BISHYDROXYCOUMARIN ™)<br>Phenprocoumon |
| Thrombin (FIIa)Inhibitors | Argatroban (NOVASTAN ®)[1]<br>Ximelgatran (EXANTA ®)[2]<br>BIBR 1048[2]<br>BIBR 953<br>Desirudin (REVASC ®)[1]<br>Lepirudin (REFLUDAN ® or PHARMION ®)[1] Bivalirudin (ANGIOMAX ®, previously HIRULOG ®)[1] |
| FXa Inhibitors | DX-9065a[2]<br>DPC 906[2]<br>Antistasin[3] |
| TF/FVIIa Inhibitors | Anti-TF antibodies<br>Recombinant Nematode Anticoagulant Protein (rNAPc2)[2]<br>Recombinat Tissue Factor Pathway Inhibitor (TIFACOGIN ™)[2]<br>FVIIai[3] |
| ART-123 ™ (recombinant soluble thrombomodulin)[2] | |

[1]FDA approved for use in humans
[2]Evaluated in clinical trials but not yet approved
[3]Still in development (animal studies only)

EXAMPLES

Varying the Ratio of Phospholipid to rTF does not Affect ISI

The purpose of this study was to identify which properties of synthetic thromboplastin reagents determine their ISI values. To do so, the composition of such reagents was systematically varied and the impact on relative ISI was measured. One of the variables that can be controlled during relipidation of rTF is the ratio of phospholipid to tissue factor. This was achieved during relipidation by holding the total phospholipid concentration constant while varying the rTF concentration. In this series of experiments, the phospholipid composition was 20 mol % PS and 80 mol % PC, and the molar ratios of total phospholipid to rTF varied over a wide range, from 1000:1 to 300,000:1. Varying the ratio of phospholipid to rTF in synthetic thromboplastin reagents had little or no effect on ISI.

Phospholipid Composition

Another variable that can be controlled in synthetic thromboplastin preparations is the phospholipid composition. Negatively charged phospholipids—most especially PS—promote optimum tissue factor activity [16]. Accordingly, we varied the phospholipid composition during rTF relipidation from 5 to 30 mol % PS, with the balance being PC. The phospholipid composition of synthetic thromboplastins had a profound effect on relative ISI, which varied essentially linearly from 0.67 to 1.55 over this range of PS content (FIG. 1).

Previously it had been shown that PE could synergize with PS in enhancing the procoagulant activity of tissue factor, dramatically decreasing the amount of PS needed to achieve maximal procoagulant activity [11]. The ability of PE to influence ISI values was investigated by relipidating rTF into phospholipid vesicles containing a constant 40 mol % PE, and varying the PS content from 1 to 15 mol % (the balance of the phospholipids was PC). As can be seen from FIG. 1, incorporating PE into relipidated rTF preparations dramatically shifted the relationship between relative ISI and mol % PS (i.e., the curve is shifted to the left). So, the same ISI value can be obtained at much lower PS levels in the presence of 40% PE than in the absence of PE. The slope of the relationship between ISI and mol % PS was also steeper, indicating that ISI values were even more sensitive to PS content in the presence of PE than in its absence. In FIG. 1 the remainder of the phospholipid in the reagents was either PC (●); or 40 mol % PE plus sufficient PC to make 100% (▲). Data points represent mean (±standard error) of relative ISI determinations from three separate synthetic thromboplastin preparations, each of which were prepared from three separate relipidations of rTF.

Figure 10:
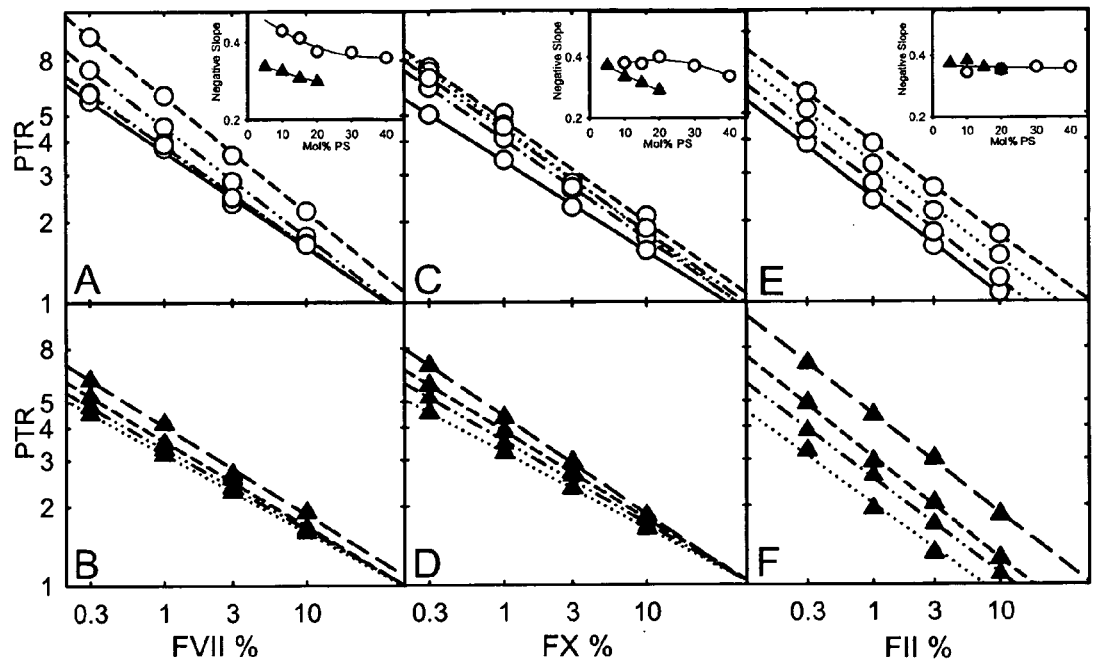
FIGS. 10 (A), (B), (C), (D), (E) and (F) are graphs of the response to factor deficiency with variable phospholipid content: (A) and (B) Factor VII deficiency; (C) and (D) Factor X deficiency; and (E) and (F) prothrombin deficiency.

Next, the phospholipid composition during rTF relipidation was varied from 10 to 40 mol % PS in the absence of PE, and from 5 to 20 mol % PS in the presence of 40 mol % PE (with the balance of the phospholipid being PC). Decreasing the PS content steepened the response curve for Factor VII and Factor X, but had no effect on the slope of the response curve for Factor II (see FIG. 10). Note that in the absence of PE, limiting PS had greater impact on the slope of the response curve for Factor VII at PS levels <20%, while the impact was greater on the response curve for Factor X when the PS level was >20%. In the presence of PE, decreasing PS steepened the slopes of the response curves for both Factor VII and Factor X over the entire range of PS evaluated. Although the slope of the response curve for Factor II deficiency was unchanged, the position of the curve was shifted upward by decreasing PS. As shown in FIG. 10, in these reagents the remainder of the phospholipid was either PC (gray circles, (A), (C) and (E)); or 40 mol % PE plus sufficient PC to make 100% (black triangles, (B), (D) and (F)). Mol % PS contents are 5% (long dash); 10% (short dash); 15% (dash dot, dot); 20% (dot); 30% (dash dot); 40% (solid line). Similar data was collected from three separate synthetic thromboplastin preparations, each of which was prepared from three separate relipidations of rTF. For simplicity, curves from a single experiment are shown.

Sensitivity to Factor VII Deficiency (FIGS. 10, (A) and (B))

Changes in the amount of PS included in the relipidation had a small effect on the position and slopes of the response to decreased amounts of Factor VII. Decreasing the relative mol % of PS, both in the absence and the presence of PE, shifted the response curve upward, and indicated a more significant prolongation of the PT by Factor VII deficiency. The slope of the response of the reagents to Factor VII deficiency was also steeper as PS content was decreased, indicating that lower amounts of PS can result in a reagent with greater ability to distinguish between minor shifts in activity of Factor VII. In the presence of PE the response curves were less steep than in the absence of PE. When PE was absent, alteration of the PS content had a more profound effect on the slope of the response curve than when PS content was <20 mol %. When PE was absent, PS contents above 20 mol % failed to impact the slope of the response curve to any significant degree.

Sensitivity to Factor X Deficiency (FIGS. 10, (C) and (D))

Changes in the amount of PS included in the relipidation also had a small impact on the position and slopes of the response to decreased amounts of Factor X. Decreasing the relative mol % of PS, both in the absence and the presence of PE, also shifted the Factor X response curve upward. This change in curve position was similar to the effect on Factor VII response curves in the presence of 40 mol % PE, but the response to Factor X deficiency was less profound in the absence of PE than was the response to Factor VII deficiency. As was noted for Factor VII, the slope of the response to Factor X deficiency was steeper as PS content was decreased. In the absence of PE the response curves were generally steeper than in the presence of PE. In the absence of PE, PS contents below 20 mol % failed to impact the slope of the response curve to any significant degree.

Sensitivity to Prothrombin Deficiency (FIG. 10, (E) and (F))

Changes in PS content most significantly impacted response to prothrombin deficiency. Decreasing the amount of PS shifted the position of the response curve describing PT prolongation upward, but the slope of the curve was unchanged. The relationship between PS content and position of the response curve was similar in the presence of 40 mol % PE, but the shift in curve position was more profound relative to the change in PS content. The lack of impact on the slope of the response curve to changes in PS content results in a similar relative sensitivity to any specific degree of prothrombin deficiency for all of the reagents, regardless of the PS content. However, the minimal level of prothrombin deficiency required to prolong the PT (PTR greater than 1) is markedly shifted by changes in PS content. Lower levels of PS cause the PT to be prolonged at higher percent of normal factor level.

Ionic Strength

Figure 2:
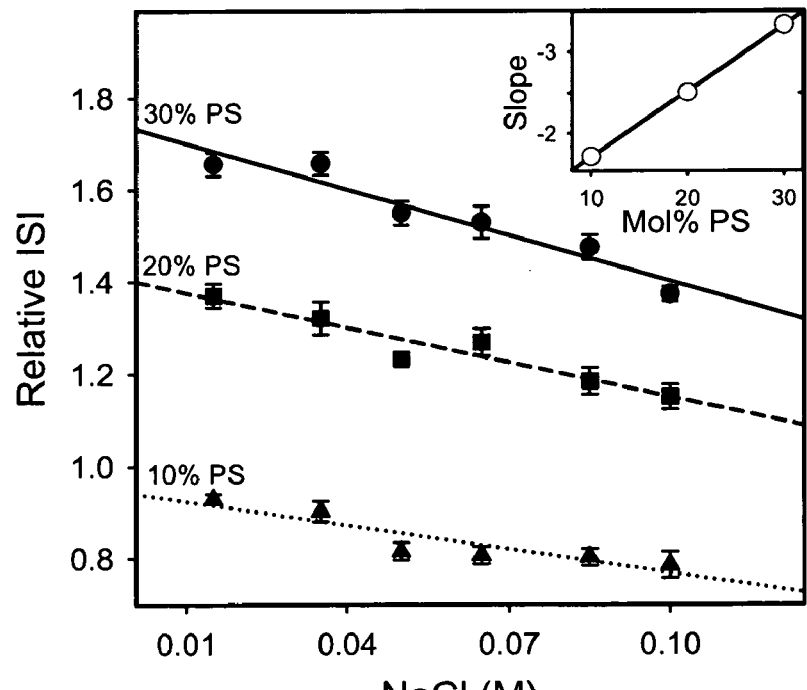
FIG. 2 is a graph of the relationship between thromboplastin sensitivity as measured by ISI and ionic strength.

Yet another variable that can be readily controlled in thromboplastin reagents is ionic strength, which we investigated by varying the NaCl concentration. As can be seen in FIG. 2, relative ISI values of synthetic thromboplastin preparations varied nearly linearly according to NaCl concentration over a range of 15 to 100 mM NaCl. The effect of ionic strength on ISI was evaluated for three different synthetic thromboplastin reagents, containing 10, 20 or 30 mol % PS. Increasing the NaCl concentration decreased the relative ISI value for each type of thromboplastin. As can be seen from the inset to FIG. 2, the slopes of the lines describing these relationships varied according to the level of PS in the reagent, showing that the ISI values of synthetic thromboplastin reagents became more sensitive to NaCl concentration as PS content increased. Overall, however, the impact of NaCl concentration on ISI was smaller than the much more dramatic impact of phospholipid composition on ISI. As shown in FIG. 2 ISI values were determined for synthetic thromboplastins made with rTF that had been relipidated into vesicles containing 10 mol % PS (▲), 20 mol % PS (■), or 30 mol % PS (●); the remainder of the phospholipid being PC (shown are the final NaCl concentrations in the reagents after mixing with the CaCl$_2$ solution). Inset: The slopes of the lines varied according to the level of PS in the reagent, showing that the ISI values of synthetic thromboplastin reagents became more sensitive to NaCl concentration as PS content increased. Data points represent mean (±standard error) of relative ISI determinations from three separate synthetic thromboplastin preparations, each of which were prepared from three separate relipidations of rTF.

Figure 11:
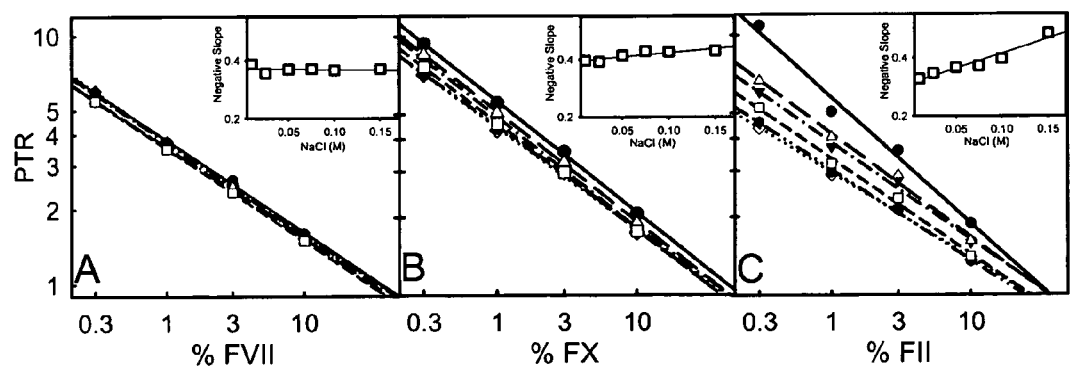
FIGS. 11 (A), (B), and (C) are graphs of the response to factor deficiency with variable NaCl concentration: (A) Factor VII deficiency; (B) Factor X deficiency; and (C) prothrombin deficiency.

To evaluate the impact of ionic strength on individual factor sensitivity, we varied the NaCl concentration in the thromboplastin reagents from 10 to 150 mM. These experiments were performed by diluting rTF relipidated into vesicles containing PC:PS at a molar ratio of 80:20. As shown in FIG. 11, in these reagents the phospholipid composition was 20 mol % PS and 80 mol % PC, while NaCl in the final reagent (after addition of the CaCl$_2$) was 10 mM (dot); 25 mM (dash dot, dot); 50 mM (short dash); 75 mM (long dash); 100 mM (dash dot); and 150 mM (solid line). Similar data was collected from three separate synthetic thromboplastin preparations, each of which was prepared from three separate relipidations of rTF. For simplicity, curves from a single experiment are shown.

Sensitivity to Factor VII Deficiency (FIG. 11A)

Varying the NaCl concentration in the prepared thromboplastin reagent had no apparent effect on the reagent's response to Factor VII deficiency.

Sensitivity to Factor X Deficiency (FIG. 11B)

Varying the NaCl concentration in the prepared thromboplastin reagent had a minor effect on the position and slope of the response curves describing response of the reagents to Factor X deficiency. Increasing NaCl content shifted the position of the response curve upward (indicating greater prolongation of PT at any given level of Factor X) and steepened the slope of the response curve (indicating greater relative sensitivity to any change in Factor X activity). However, the effect of changes in NaCl concentration on Factor X response curves was minor.

Sensitivity to Factor II Deficiency (FIG. 11C)

Varying the NaCl concentration in the prepared thromboplastin reagent had the most profound effect on the response curves describing response of the reagents to Factor II deficiency. Increasing NaCl content markedly steepened the slope of the response curve. Higher NaCl concentration resulted in reagents with greater relative sensitivity to any change in level of Factor II.

Factor Response and Relationship to ISI and INR

Because ISI is currently the accepted overall measure of a thromboplastin reagent's response to deficits in the coagulation factors of the extrinsic pathway, we wanted to relate the response curves described above to the ISI's measured for each reagent. The response curves represent variable responses of 2 types: relative importance of the individual factor at any given percent of normal level, and slope of the response. Because the slopes are variable, in some cases there would be a more profound difference between the response to comparable depletion of the three vitamin K dependent factors when factor levels were lower rather than when factor levels were higher. We chose to compare the reagents at a specific level of factor activity, by comparing the PTR at 10% of each individual factor and the PTR at 1% of each individual factor determined from the regression line.

As would be expected, lower ISI reagents responded more significantly at 10% normal factor level for all 3 factors than did higher ISI reagents, regardless of the composition of the reagent. However, the relative sensitivity between Factor VII, Factor X, and Factor II to 10% normal factor level was markedly different depending on the reagent composition. When the reagent ISI is adjusted to ISI about 1.0 by decreasing the amount of net negatively charged phospholipids, at 10% factor levels the relative emphasis on response to factor depletion is similar for all 3 factors (slightly greater for Factor X). However, adjustment of the ISI to about 1.0 by changing the NaCl content in the reagent results in a reagent with greatest sensitivity to Factor X, followed by Factor II, and lastly by Factor VII.

The differences in response to the various factors is further magnified at 1% of normal factor level. In reagents made with variable PS content in the absence of PE (FIG. 3B), decreasing the ISI resulted in greater response to all 3 factors. However, the lowest ISI reagents emphasized response to Factor VII over that to Factor X, whereas response to Factor X was emphasized in reagents of higher relative ISI. Reagents of relative ISI of about 1.0 responded most significantly to Factor X, followed closely by Factor VII, and then responded to a much lesser degree to Factor II.

In reagents made with variable PS content in the presence of 40 mol % of PE (FIG. 3A), decreasing the ISI (by decreasing the PS content) resulted in additional emphasis on response to Factor II and to a lesser extent on Factor VII. The measured PTR at 1% Factor II with a reagent of ISI 1.0 would be more than double that measured with a reagent of relative ISI 1.8. Furthermore, as was seen for reagents made without PE, the lowest ISI reagents actually responded more significantly to 1% normal level of Factor VII than to an identical level of Factor X, whereas response to Factor X was relatively more important in reagents of higher relative ISI. However, reagents of relative ISI of about 1.0 responded similarly to all 3 factors, with order of level of response of Factor VII>Factor X>Factor II.

In reagents made with variable NaCl content (FIG. 3C), a lower ISI was associated with a higher response Factor X and Factor II, but essentially no change in response to Factor VII. The change in Factor II response was quite profound over the range of salt content evaluated. The low ISI (from high salt) of these reagents is due to a drastic increase in response to Factor II deficiency. Reagents of relative ISI of about 1.0 responded most significantly to Factor X, followed closely by Factor II, and then Factor VII.

Figure 3:
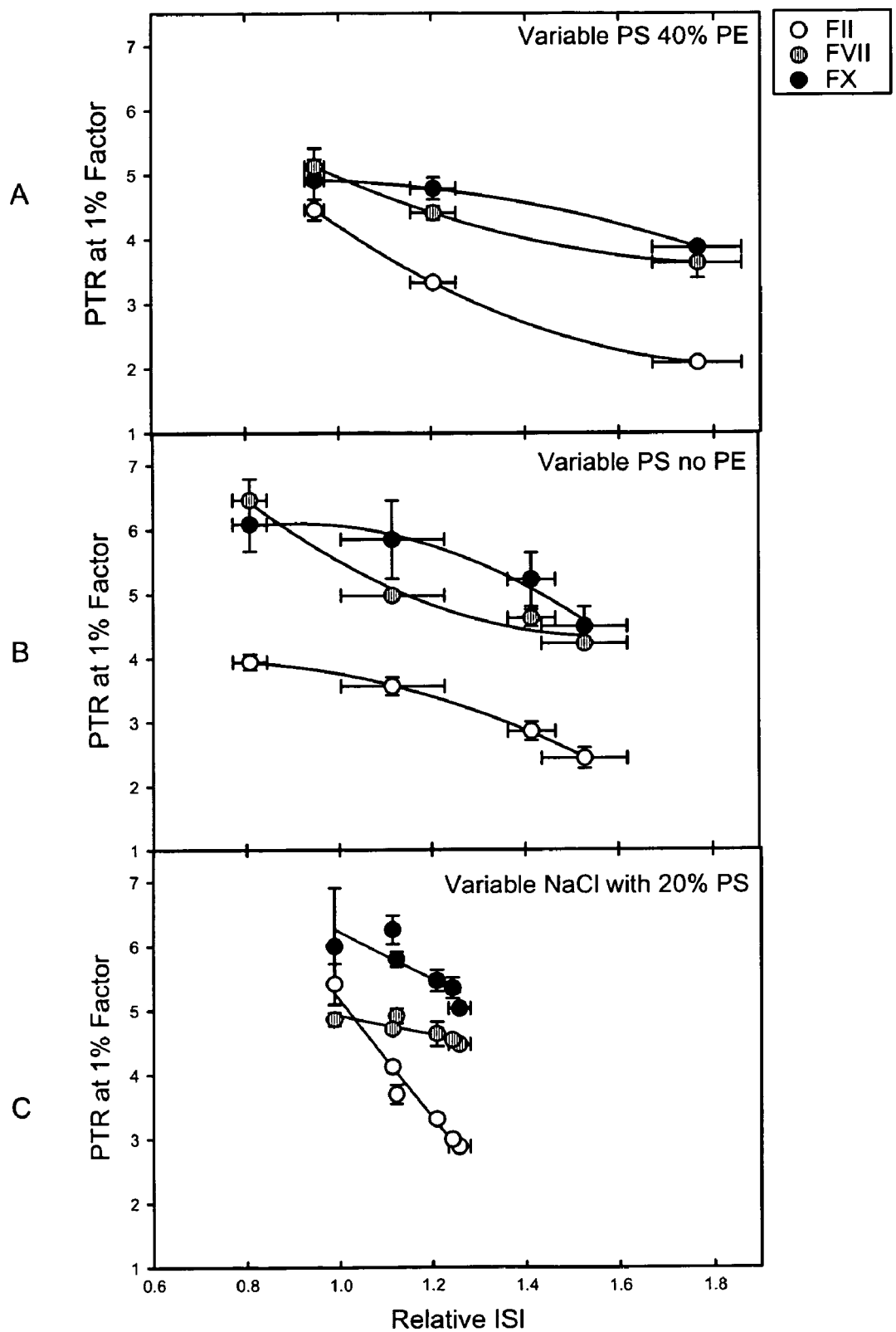
FIGS. 3 (A), (B) and (C) are graphs of the relationship between thromboplastin sensitivity as measured by ISI and response to individual factor deficiencies: (A) variable PS with 40% PE; (B) variable PS with no PE; (C) variable NaCl concentration with 20% PS (individual factor response as compared to ISI at 1% normal factor levels).

In FIG. 3, panel B describes reagents made by varying PS content in the absence of PE and diluted in buffer containing 100 mM NaCl; panel A describes reagents in the same buffer, but made by varying PS content in the presence of 40% PE; and panel C describes reagents made with 20 mol % PS but variable NaCl content in the suspension buffer. Measured PTR in response to depletion of Factor VII (gray circles), Factor X (black circles) and Factor II (white circles) is reported. Data points represent mean (±standard error) from three separate synthetic thromboplastin preparations, each of which were prepared from three separate relipidations of rTF.

Effect of Addition of Factor VIIa to Thromboplastins

Figure 5:
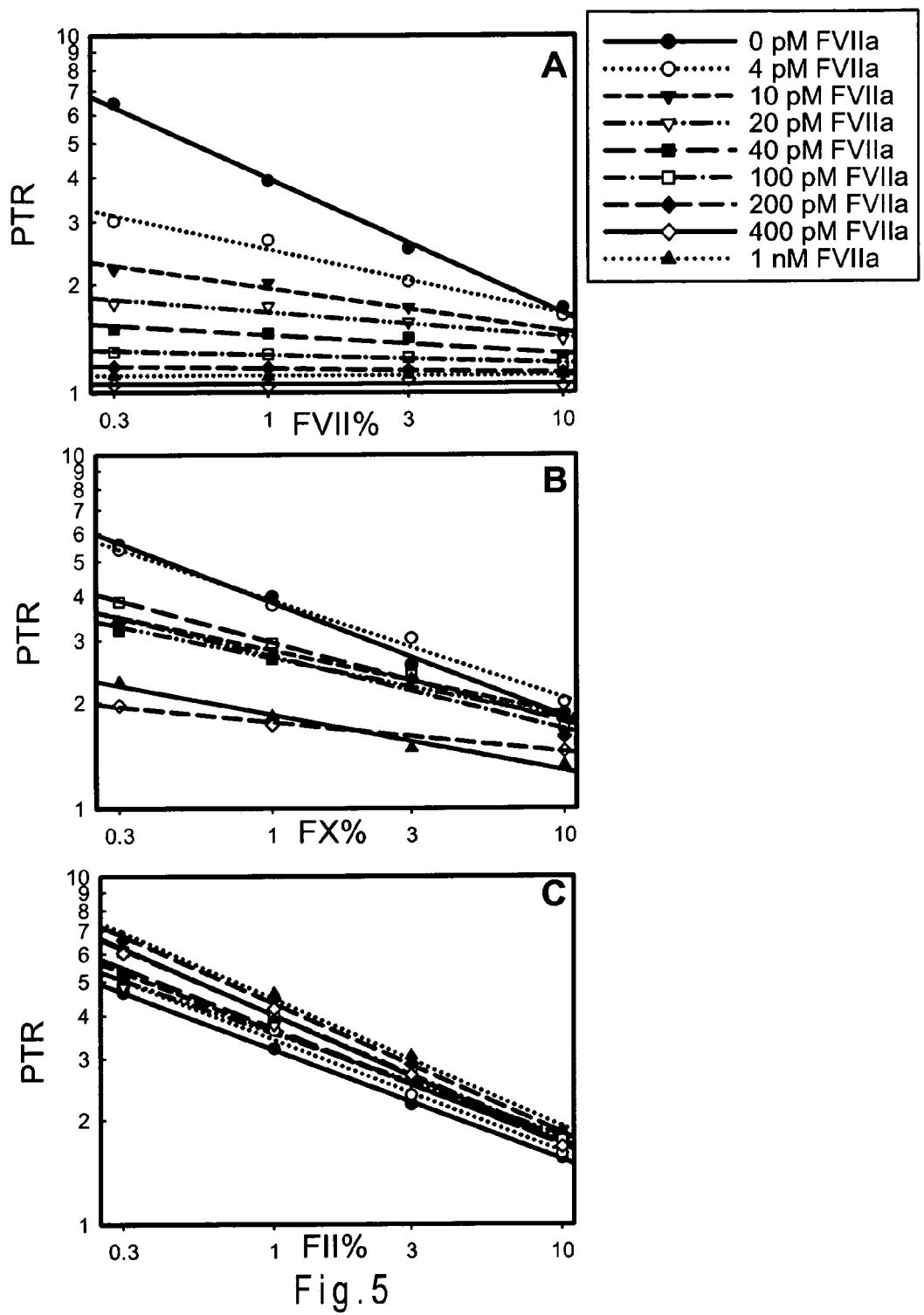
FIGS. 5 (A), (B) and (C) are graphs of the response of reagents containing 20 mol % PS and 50 mM NaCl to deficiencies of Factors VII, X, and prothrombin when Factor VIIa is added to the reagent: (A) Factor VII response; (B) Factor X response; and (C) prothrombin response.

Initial experiments employed TF relipidated into vesicles containing 20 mol % PS; 80 mol % PC suspended in TBSA containing 100 mM NaCl (50 mM final NaCl after the addition of 25 mM $CaCl_2$ to the reagent). Factor VIIa was added to the reagents at levels of 4–1000 pM. Response curves for the three vitamin K dependent factors are reported in FIG. 5.

Figure 6:
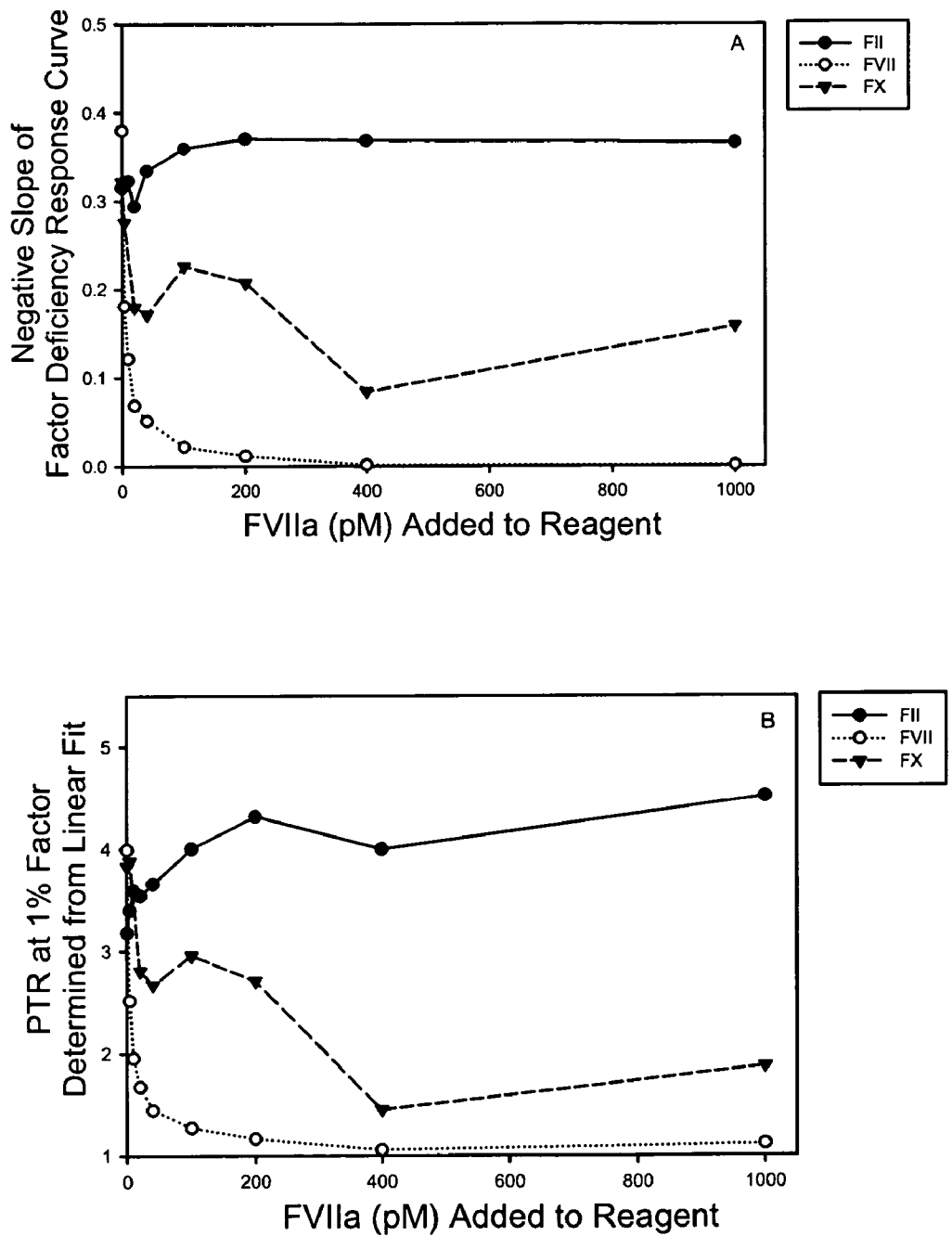
FIGS. 6 (A) and (B) are graphs of the change in the response to factors with the addition of Factor VIIa in reagents containing 20 mol % PS with 50 mM final reagent NaCl: (A) Change in the negative slope of the response curve (a measure of the relative response to worsening factor deficiency); and (B) Change in PTR at 1% factor (a clinically relatable number indicating degree of prolongation of the PT).

As expected, Factor VIIa spiking decreased response of the reagents to deficiency of Factor VII (FIG. 5a). The negative slope of the response curve gradually decreased as Factor VIIa levels were increased, until the negative slope was essentially 0, indicating no prolongation of the PT despite worsening Factor VII deficiency in the plasma samples evaluated (FIG. 6a). At Factor VIIa levels greater than 200 pM in the reagent, response to worsening Factor VII deficiency was essentially completely eliminated. This indicates that even for samples with profound Factor VII deficiency, the PT would not be significantly prolonged to a PTR above 1.0 (FIG. 6b).

Interestingly, addition of Factor VIIa to the reagent also had an impact on response to Factor X. Addition of Factor VIIa decreased response to Factor X, but to a less profound degree than for the response to Factor VII (FIG. 5b). Any addition of Factor VIIa lessened the responsiveness of the reagent to Factor X deficiency, but small amounts (<40 pM) markedly decreased the negative slope of the response curve and higher amounts (>100 pM Factor VIIa) had a less profound effect on the curve (FIG. 6a).

Addition of Factor VIIa to the reagent had the opposite effect on response to prothrombin deficiency, with increasing amounts of Factor VIIa resulting in a mildly increased responsiveness to prothrombin deficiency (FIGS. 5c and 6a).

Additional experiments using TF relipidated into vesicles containing 10 mol % PS; 40 mol % PE; 50 mol % PC suspended in TBSA containing 100 mM NaCl (50 mM final NaCl after the addition of 25 mM $CaCl_2$ to the reagent) resulted in factor response curves similar to those obtained with reagent containing 20 mol % PS. The impact of various levels of Factor VIIa added to the reagent was similar (data not shown).

Figure 4:
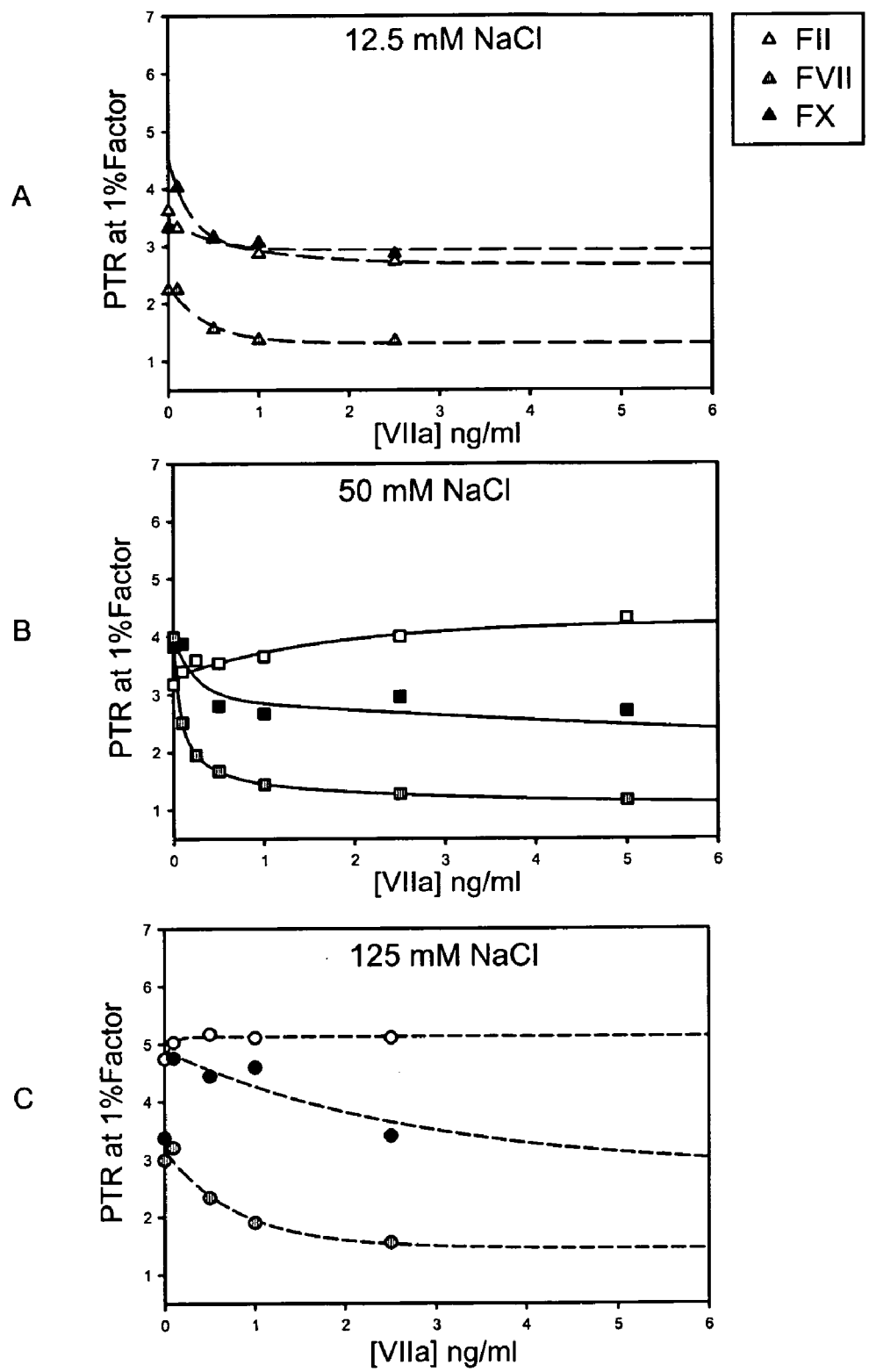
FIGS. 4 (A), (B) and (C) are graphs of the relationship between response to individual factor deficiency and Factor VIIa added to the reagent: (A) 12.5 mM NaCl; (B) 50 mM NaCl; (C) 125 mM NaCl.
Figure 7:
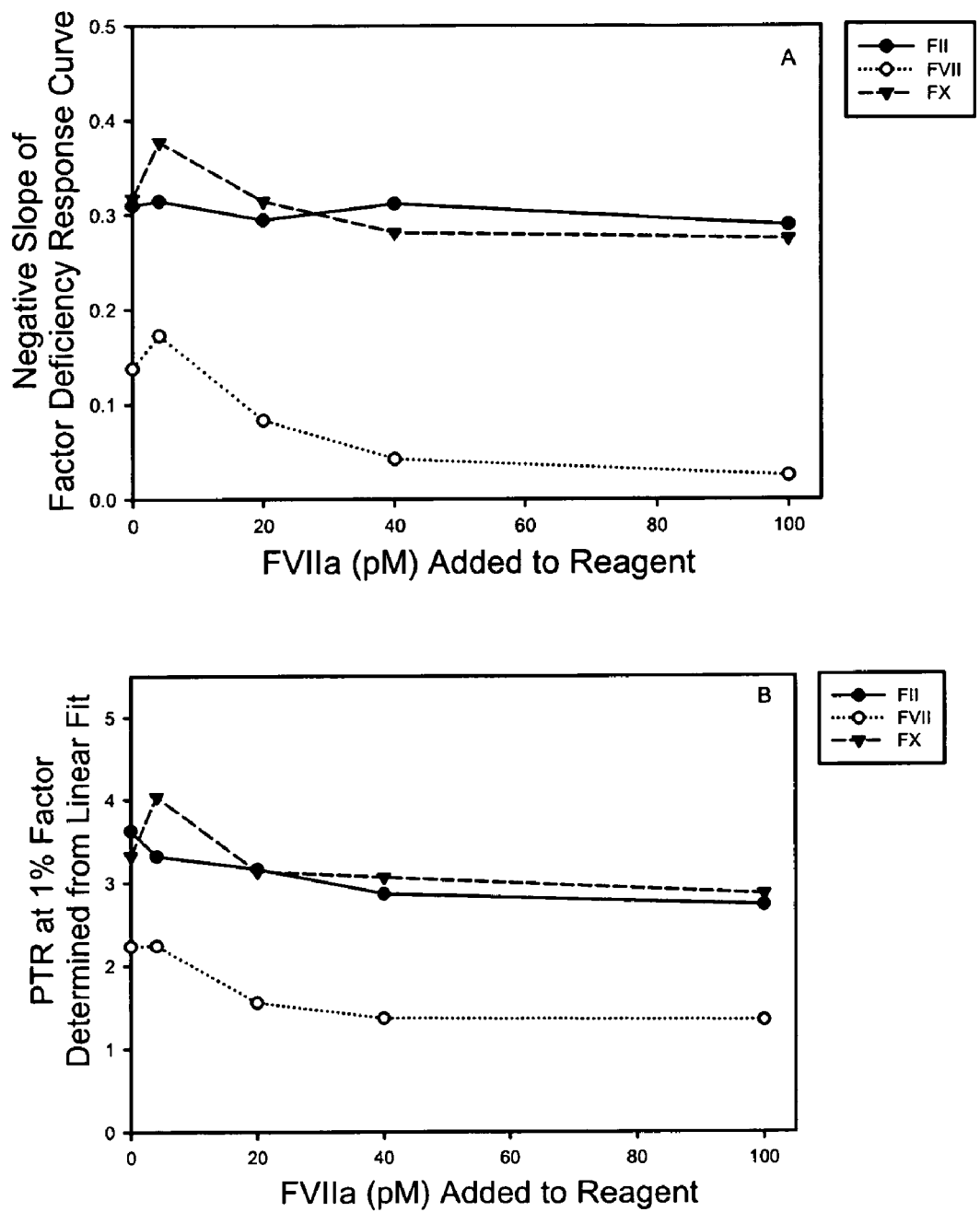
FIGS. 7 (A) and (B) are graphs of the change in the response to factors with the addition of Factor VIIa in reagents containing 20 mol % PS with 12.5 mM final reagent NaCl: (A) Change in the negative slope of the response curve; and (B) Change in PTR at 1% factor.
Figure 8:
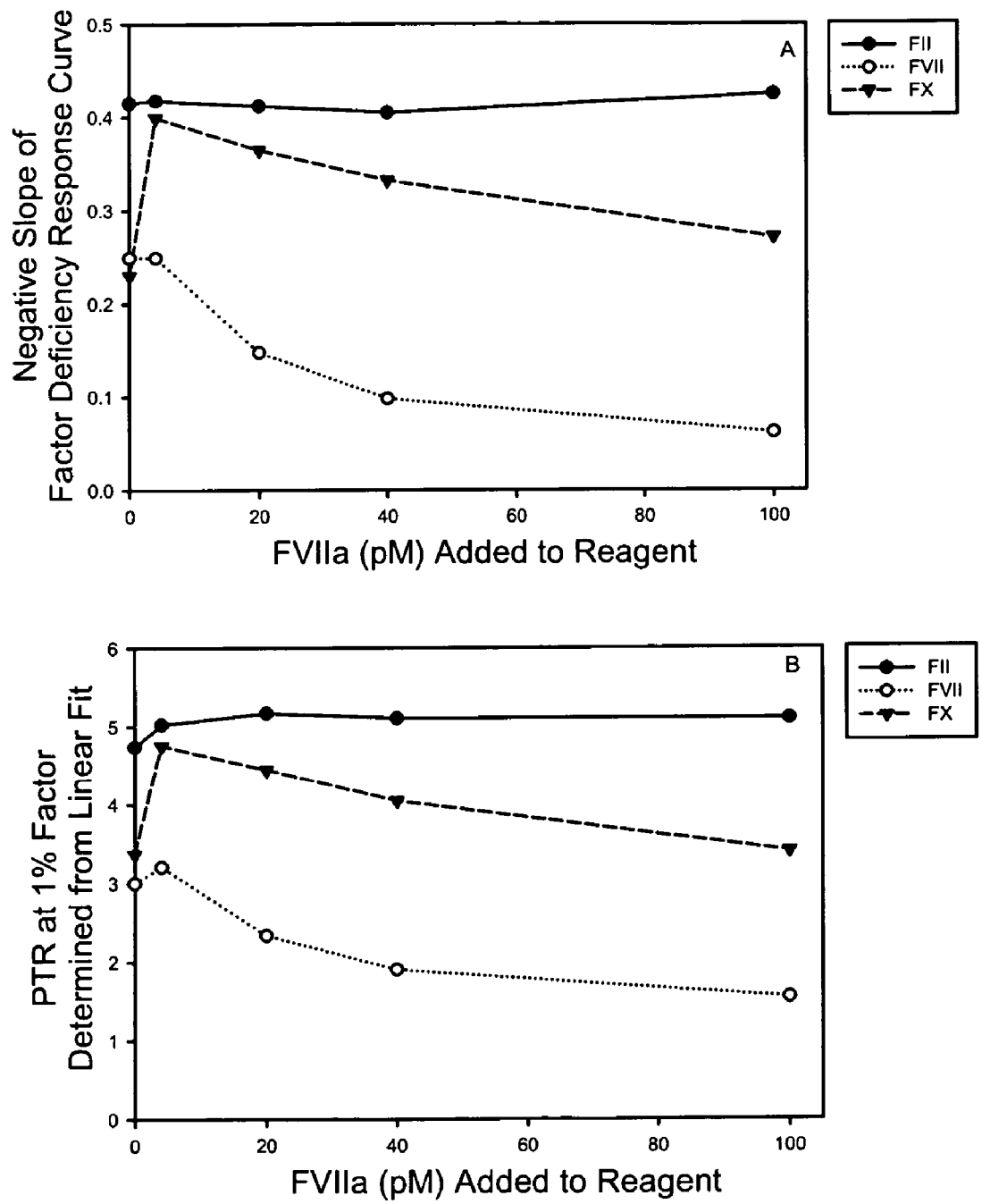
FIGS. 8 (A) and (B) are graphs of the change in the response to factors with the addition of Factor VIIa in reagents containing 20 mol % PS with 125 mM final reagent NaCl: (A) Change in the negative slope of the response curve; and (B) Change in PTR at 1% factor.
Figure 9:
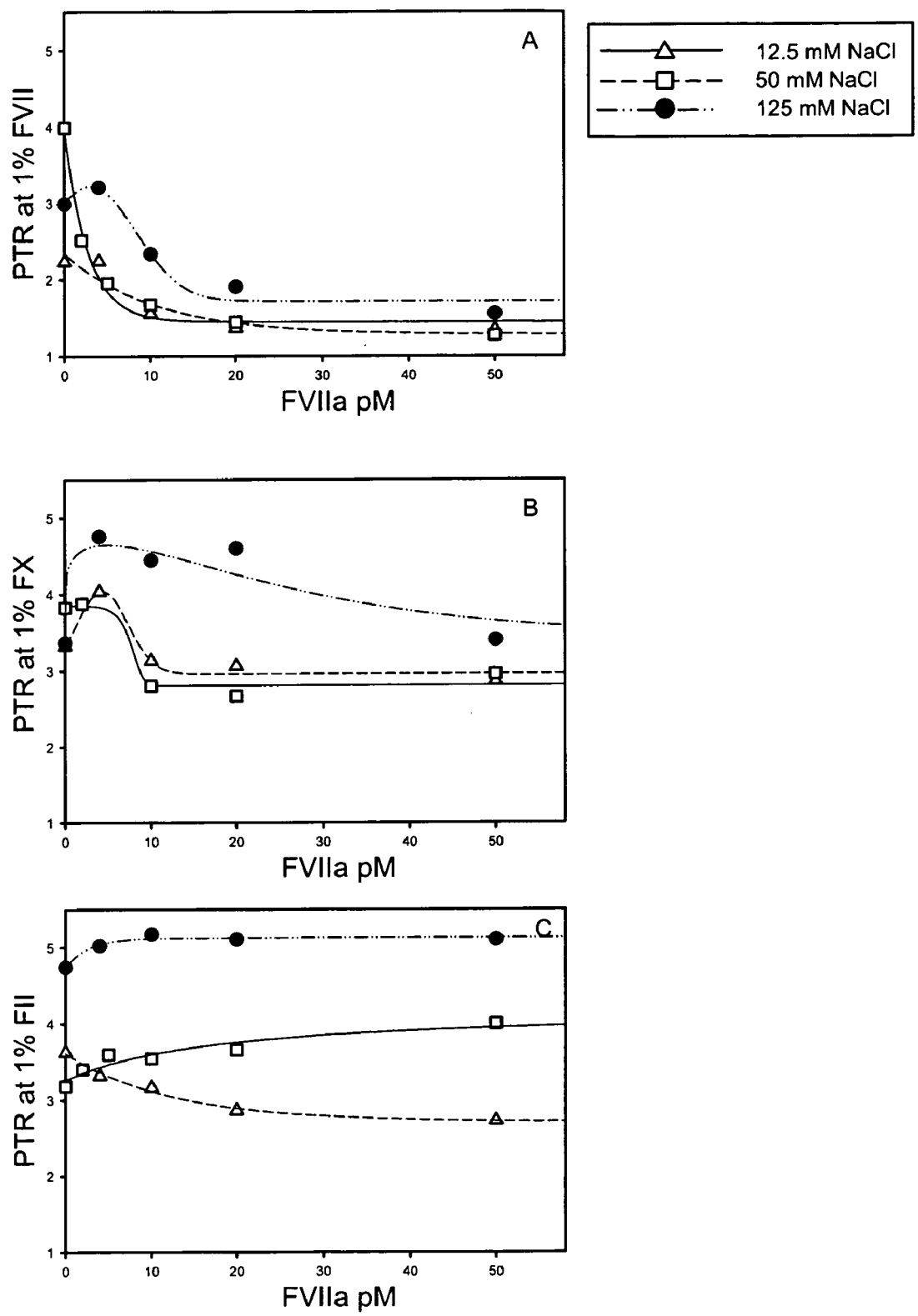
FIGS. 9 (A), (B) and (C) are graphs of the response (as measured by PTR at 1% factor) of reagents with various salt concentrations plotted for each factor individually: (A) Factor VII response; (B) Factor X response; and (C) Factor II response.

When the thromboplastin reagent was made with 20 mol % PS but the NaCl concentration in the suspension buffer was changed to either 25 mM or 250 mM (12.5 mM or 125 mM after the addition of 25 mM $CaCl_2$ to the reagent), the impact of spiking the reagent with Factor VIIa was different than for a reagent containing a more physiologic salt concentration. As compared to reagents made with 100 mM NaCl (50 mM after the addition of 25 mM $CaCl_2$ to the reagent), spiking reagents containing the low salt concentration with Factor VIIa had a less profound impact on response to Factor VII and minimized the effects of Factor VIIa addition on response to Factor X and prothrombin (FIGS. 7 and 8). As compared to reagents made with 100 mM NaCl, spiking reagents containing the high salt concentration with Factor VIIa had a less profound impact on response to Factor VII, a reversed impact on response to Factor X (adding Factor VIIa increased rather than decreased responsiveness) and no impact on response to prothrombin (FIGS. 4 and 9).

EXPERIMENTAL DETAILS

Purified egg phosphatidylcholine (PC), bovine brain phosphatidylserine (PS), and bovine liver phosphatidylethanolamine (PE) from Avanti Polar Lipids (Alabaster, Ala.) were stored in chloroform under nitrogen at −20° C. Octaethylene glycol monododecyl ether (C12E8) was from Fluka (Sigma-Aldrich, St. Louis, Mo.); HEPES and bovine serum albumin were from Calbiochem (La Jolla, Calif.); and Bio-Beads® SM-2 were from Bio-Rad (Hercules, Calif.). Citrated normal human plasma pooled from 31 individuals (16 men and 15 women, aged 18–56 years) and individual plasmas from patients treated with COUMADIN® (spanning a range of INR values) were obtained from George King Biomedical (Overland Park, Kans.). Plasma immunodepleted of individual coagulation Factors II, VII, and X was obtained from Biopool International (Ventura, Calif.). Hemoliance RecombiPlasTin was from Instrumentation Laboratory (Lexington, Mass.). Recombinant human Factor VIIa was obtained from American Diagnostica (Stamford, Conn.).

The commercially-available, recombinant human thromboplastin reagent used in this study was Hemoliance RecombiPlasTin (Instrumentation Laboratory, Lexington, Mass.), lot number N092867, which was reconstituted and used according to the manufacturer's instructions. According to the manufacturer, the ISI for this lot of thromboplastin was 0.94 for the type of coagulometer used in this study.

Recombinant, membrane-anchored human tissue factor (rTF) was expressed in *E. coli* and purified essentially as previously described [11]. This version of rTF consists of amino acids 1–244 [12], which includes the entire extracellular and transmembrane domains, and the first two amino acids of the cytoplasmic domain. It also has a short peptide epitope (AEDQVDPRLIDGKS) on its amino terminus for affinity purification using immobilized HPC4 antibody. Numerous experiments have shown that the presence of this short peptide on the amino terminus has no effect on rTF function [13].

Determination of Relative ISI

The method recommended by the WHO for determining ISI values of thromboplastins involves the comparison of clotting times (measured by the manual tilt-tube method) obtained with a WHO reference thromboplastin and clotting times obtained with the test thromboplastin, for a collection of freshly isolated plasmas from sixty patients stably anticoagulated on COUMADIN® and twenty normal individuals [5]. A log-log plot of clotting times is then prepared for each thromboplastin and the ISI value is derived from the slope of the orthogonal regression line from this plot, multiplied by the ISI value of the reference thromboplastin [5]. Due to the complexity of this procedure, some investigators have successfully used a simplified approach, using a smaller number of lyophilized plasmas, for determining ISI values of thromboplastin reagents [15]. Since our investigations have necessitated the determination of many hundreds of ISI values for our synthetic thromboplastin reagents, neither the full WHO method nor the more simplified method were practical. We therefore developed a further simplified method for determining what we have termed "relative ISI" values. In this method, we have used a commercial thromboplastin of known ISI (RecombiPlasTin) as the reference thromboplastin, and have used frozen plasma samples consisting of pooled normal plasma and plasmas from five patients who are anticoagulated with COUMADIN® and who have a distribution of INR values. Orthogonal linear regression of log-log plots of the clotting times obtained with the two thromboplastins are then multiplied by the ISI value of the reference thromboplastin, yielding the "relative ISI" value. While these relative ISI values may not be precisely the same as ISI values obtained using the WHO method, we have found that they are sufficient to indicate how ISI values vary in synthetic thromboplastin reagents. It should be noted that "relative ISI" as determined by this method is not identical to ISI determined by the WHO method and should not be used for management of patients receiving anticoagulant medication. The absolute ISI value of the thromboplastin reagent should be determined by the WHO approved method.

Reconstitution of rTF into Vesicles

Reconstitution of rTF into phospholipid vesicles was by the rapid Bio-Bead method as previously described [14]. Reconstitution was by the "Standard Method" described therein, using 10 mM $C_{12}E_8$ to initially dissolve the phospholipids, with the following variations: Some relipidations employed variable proportions of PC, PE and PS, although the total phospholipid concentration was held constant at 2.6 mM; and some relipidations employed variable concentrations of rTF. Unless otherwise stated, relipidated rTF preparations contained these final concentrations: 300 nM rTF, 2.6 mM total phospholipids, 20 mM HEPES-NaOH pH 7.5, 25–250 mM NaCl, 0.02% $NaN_3$. The typical molar ratio of phospholipid to rTF in the final product was therefore approximately 8700:1. Relipidated rTF preparations were stored at 4° C.

Synthetic thromboplastin reagents were prepared by first diluting relipidated rTF with TBSA, yielding rTF concentrations that ranged from 2.7 nM to 103 nM. (TBSA=50 mM Tris-HCl pH 7.4, 25–250 mM NaCl, 0.1% bovine serum albumin, 0.02% $NaN_3$.) Diluted rTF preparations were then mixed with equal volumes of 25 mM $CaCl_2$ and used in the clotting assay. For each synthetic thromboplastin, the concentration of relipidated rTF was chosen to yield a 12–15 s clotting time with pooled normal plasma. When this was not possible, the dilution yielding the shortest achievable clotting time with pooled normal plasma was chosen. In some experiments reagents were spiked with variable concentrations of purified recombinant Factor VIIa.

Clotting Assay

Prothrombin Time (PT) clotting assays were typically performed using an ST4 coagulometer (Diagnostica Stago, Parsippany, N.J.). A 50 μL plasma sample was incubated in a cuvette for 2 min at 37° C., after which clotting was initiated by adding 100 μL pre-warmed (37° C.) thromboplastin reagent, and the time to clot formation was measured. PT assays were typically performed in duplicate for each sample.

Determination of Relative ISI

For each thromboplastin preparation to be tested, clotting times were determined by PT assay for pooled normal plasma and for plasma samples from five different patients who were anticoagulated with COUMADIN®. The reference thromboplastin was RecombiPlasTin, while the test thromboplastins were various formulations of synthetic thromboplastins described above. A log-log plot was prepared of clotting times obtained with reference thromboplastin (y-axis) versus clotting times obtained with test thromboplastin (x-axis), and a line was fitted to the data points by orthogonal regression using SigmaPlot (SPSS, Chicago, Ill.). The relative ISI of the test thromboplastin was defined as the slope of the orthogonal regression line multiplied by 0.94, which was the ISI of this lot of RecombiPlasTin.

Patient Plasmas

INR values for the plasmas of patients who were anticoagulated with COUMADIN® were determined using RecombiPlasTin, by dividing the clot time of the patient sample by the mean clot time of 20 normal plasmas, and raising the ratio to a power of 0.94. (Table 2)

Patient samples were further evaluated by measuring their levels of individual clotting factors. To produce standards, pooled normal plasma was diluted into imidazole buffer (50 mM imidazole, 100 mM NaCl, pH 7.4) to 0.5 to 20% of normal. Patient samples were diluted 5-, 10-, and 20-fold in imidazole buffer. A 50 μL diluted plasma sample or standard was added to 50 μL factor deficient plasma (Factors VII, X, V, and II) and incubated in a cuvette for 2 min at 37° C., after which clotting was initiated by adding 100 μL pre-warmed RecombiPlasTin reagent, and the time to clot formation was measured. Assays were performed in duplicate for each sample. A log-log plot was prepared of clotting times (y-axis) versus % factor (x-axis), and a line was fitted to the data points by linear regression using SigmaPlot. Factor levels as a percent of normal were determined in reference the standard curve. Fibrinogen levels were determined using Fibrotek Fib ($r^2$ diagnostics, South Bend, Ind.).

TABLE 2

Properties of the plasma samples from patients on COUMADIN ® that were used to determine relative ISI.

| | | Individual clotting factor levels* | | | | |
|---|---|---|---|---|---|---|
| Patient | INR | Factor VII | Factor X | Prothrombin | Factor V | Fibrinogen (mg/dL) |
| 1 | 3.03 | 48.1 | 26.7 | 36.6 | 114.5 | 537 |
| 2 | 3.17 | 20.4 | 21.1 | 17.4 | 74.5 | 1160 |
| 3 | 4.44 | 9.4 | 5.7 | 5.7 | 107.7 | 308 |

TABLE 2-continued

Properties of the plasma samples from patients on COUMADIN ® that were used to determine relative ISI.

| Patient | INR | Individual clotting factor levels* | | | | |
|---|---|---|---|---|---|---|
| | | Factor VII | Factor X | Prothrombin | Factor V | Fibrinogen (mg/dL) |
| 4 | 4.87 | 9.8 | 4.2 | 4.1 | 82.0 | 269 |
| 5 | 5.56 | 14.1 | 4.0 | 6.5 | 114.5 | 592 |

*The levels of individual clotting factors (except for fibrinogen) are reported as percent of the level in pooled normal plasma.

Clotting Assay for Evaluation of Response to Factor Deficits

Pooled normal plasma was diluted into factor deficient plasma to result in samples containing 10%, 3%, 1%, and 0.3% normal factor levels. PT clotting assays were performed using an ST4 coagulometer (Diagnostica Stago, Parsippany, N.J.). A 50 µL plasma sample was incubated in a cuvette for 2 min at 37° C., after which clotting was initiated by adding 100 µL of pre-warmed thromboplastin reagent, and the time to clot formation was measured. PT assays were performed in duplicate for each sample.

A prothrombin time ratio (PTR) was determined by dividing the PT for the factor deficient sample by the PT for pooled normal plasma (100% factor) obtained with the same thromboplastin reagent. A log-log plot was then prepared of PTR (y-axis) versus the percent normal factor level (x-axis). A line was fitted to the data points by linear regression using Sigma Plot (SPSS, Chicago, Ill.). The response of each thromboplastin to a given factor deficiency (a representation of the position of the regression line) was evaluated by comparing the PTR at 1% factor determined from the regression line.

REFERENCES

1 Hirsh J, Fuster V, Ansell J, Halperin J L. American Heart Association/American College of Cardiology Foundation guide to warfarin therapy. *Circulation* 2003; 107:1692–1711.
2 Morrissey J H. Tissue factor: an enzyme cofactor and a true receptor. *Thromb Haemost* 2001; 86:66–74.
3 Massignon D, Moulsma M, Bondon P, Debize G, Abidi H, Buttin T, Bon C, Pillonchery G, Coeur P. Prothrombin time sensitivity and specificity to mild clotting factor deficiencies of the extrinsic pathway: evaluation of eight commercial thromboplastins. *Thromb Haemost* 1996; 75:590–594.
4 Kitchen S, Jennings I, Woods T A, Walker I D, Preston F E. Two recombinant tissue factor reagents compared to conventional thromboplastins for determination of international normalised ratio: a thirty-three-laboratory collaborative study. The Steering Committee of the UK National External Quality Assessment Scheme for Blood Coagulation. *Thromb Haemost* 1996; 76:372–376.
5 Van Den Besselaar A M, Tripodi A, Poller L. WHO guidelines for thromboplastins and plasma used to control oral anticoagulation therapy. Annex 3. *World Health Organ Tech Rep Ser* 1999; 889: 64–93.
6 Kitchen S, Preston F E. Standardization of prothrombin time for laboratory control of oral anticoagulant therapy. *Semin Thromb Hemost* 1999; 25:17–25.
7 Bader R, Mannucci P M, Tripodi A, Hirsh J, Keller F, Solleder E M, Hawkins P, Peng M, Pelzer H, Teijidor L M, et al. Multicentric evaluation of a new PT reagent based on recombinant human tissue factor and synthetic phospholipids. *Thromb Haemost* 1994; 71:292–299.
8 Roussi J, Drouet L, Samama M, Sie P. French multicentric evaluation of recombinant tissue factor (recombiplastin) for determination of prothrombin time. *Thromb Haemost* 1994; 72:698–704.
9 Watson C, Kitchen S, Woolley A M, Young L, Malia R G. Recombinant and tissue extract thromboplastins for determination of international normalised ratio in over-anticoagulated patients. *Br J Biomed Sci* 1999; 56:123–127.
10 Testa S, Morstabilini G, Fattorini A, Galli L, Denti N, D'Angelo A. Discrepant sensitivity of thromboplastin reagents to clotting factor levels explored by the prothrombin time in patients on stable oral anticoagulant treatment: impact on the international normalized ratio system. *Haematologica* 2002; 87:1265–1273.
11 Neuenschwander P F, Bianco-Fisher E, Rezaie A R, Morrissey J H. Phosphatidylethanolamine augments factor VIIa-tissue factor activity: enhancement of sensitivity to phosphatidylserine. *Biochemistry* 1995; 34:13988–13993.
12 Morrissey J H, Fakhrai H, Edgington T S. Molecular cloning of the cDNA for tissue factor, the cellular receptor for the initiation of the coagulation protease cascade. *Cell* 1987; 50:129–135.
13 Rezaie A R, Fiore M M, Neuenschwander P F, Esmon C T, Morrissey J H. Expression and purification of a soluble tissue factor fusion protein with an epitope for an unusual calcium-dependent antibody. *Protein Expr Purif* 1992; 3:453–460.
14 Smith S A, Morrissey J H. Rapid and efficient incorporation of tissue factor into liposomes. *J Thromb Haemost* 2004; 2:1155–1162.
15 Poller L, Barrowcliffe T W, Van Den Besselaar A M, Jespersen J, Tripodi A, Houghton D. Minimum lyophilized plasma requirement for ISI calibration. European Concerted Action on Anticoagulation. *Am J Clin Pathol* 1998; 109:196–204.
16 Zwaal R F. Membrane and lipid involvement in blood coagulation. *Biochim Biophys Acta* 1978; 515:163–205.
17 Kemball-Cook G, Garner I, Imanaka Y, Nishimura T, O'Brien D P, Tuddenham E G, McVey J H. High-level production of human blood coagulation factors VII and XI using a new mammalian expression vector. *Gene.* 1994 Feb. 25; 139(2):275–279.

The invention claimed is:

1. A thromboplastin reagent, comprising:
 (a) Tissue-factor,
 (b) Factor-seven, and
 (c) a net negatively charged phospholipid,
 wherein the thromboplastin reagent is a synthetic thromboplastin reagent, and
 the thromboplastin reagent is in dried form.

2. The thromboplastin reagent of claim 1, further comprising $Ca^{2+}$.

3. The thromboplastin reagent of claim 1, further comprising phosphatidylserine.

4. The thromboplastin reagent of claim 1, further comprising at least one alkali metal salt.

5. The thromboplastin reagent of claim 1, having an International Sensitivity Index of at most 1.5.

6. The thromboplastin reagent of claim 1, having an International Sensitivity Index of 0.8 to 1.5.

7. The thromboplastin reagent of claim 1, having a prothrombin time ratio for 1% Factor VII of at most 1.5.

8. The thromboplastin reagent of claim 1, having a prothrombin time ratio for 1% Factor VII of at most 1.2.

9. The thromboplastin reagent of claim 1, having a prothrombin time ratio for 1% Factor II of at least 2.

10. The thromboplastin reagent of claim 1, having a prothrombin time ratio for 1% Factor II of at least 5.

11. The thromboplastin reagent of claim 1, wherein the Tissue-factor is r-tissue-factor.

12. The thromboplastin reagent of claim 1, wherein the Factor-seven is human Factor VIIa.

13. The thromboplastin reagent of claim 1, wherein the Factor-seven is present in an amount of at least 150 pM Factor VIIa equivalents.

14. The thromboplastin reagent of claim 1, wherein the Factor-seven is present in an amount of at least 200 pM Factor VIIa equivalents.

15. A thromboplastin reagent, comprising:
(a) Tissue-factor,
(b) Factor-seven, and
(c) a net negatively charged phospholipid,
wherein the thromboplastin reagent is a synthetic thromboplastin reagent,
the thromboplastin reagent is in dried form, and
the thromboplastin reagent does not comprise Factor II nor Factor X.

16. The thromboplastin reagent of claim 15, further comprising $Ca^{2+}$.

17. The thromboplastin reagent of claim 15, further comprising phosphatidylserine.

18. The thromboplastin reagent of claim 15, further comprising at least one alkali metal salt.

19. The thromboplastin reagent of claim 15, having an International Sensitivity Index of at most 1.5.

20. The thromboplastin reagent of claim 15, having an International Sensitivity Index of 0.8 to 1.5.

21. The thromboplastin reagent of claim 15, having a prothrombin time ratio for 1% Factor VII of at most 1.5.

22. The thromboplastin reagent of claim 15, having a prothrombin time ratio for 1% Factor VII of at most 1.2.

23. The thromboplastin reagent of claim 15, having a prothrombin time ratio for 1% Factor II of at least 2.

24. The thromboplastin reagent of claim 15, having a prothrombin time ratio for 1% Factor II of at least 5.

25. The thromboplastin reagent of claim 15, wherein the Tissue-factor is r-tissue-factor.

26. The thromboplastin reagent of claim 15, wherein the Factor-seven is human Factor VIIa.

27. The thromboplastin reagent of claim 15, wherein the Factor-seven is present in an amount of at least 150 pM Factor VIIa equivalents.

28. The thromboplastin reagent of claim 15, wherein the Factor-seven is present in an amount of at least 200 pM Factor VIIa equivalents.

29. A thromboplastin reagent, comprising:
(a) Tissue-factor,
(b) 1–1 000 pM Factor VIIa equivalents of Factor-seven, and
(c) a net negatively charged phospholipid,
wherein the thromboplastin reagent is a synthetic thromboplastin reagent and
the thromboplastin reagent is in dried form.

30. The thromboplastin reagent of claim 29, further comprising $Ca^{2+}$.

31. The thromboplastin reagent of claim 29, further comprising phosphatidylserine.

32. The thromboplastin reagent of claim 29, further comprising at least one alkali metal salt.

33. The thromboplastin reagent of claim 29, having an International Sensitivity Index of at most 1.5.

34. The thromboplastin reagent of claim 29, having an International Sensitivity Index of 0.8 to 1.5.

35. The thromboplastin reagent of claim 29, having a prothrombin time ratio for 1% Factor VII of at most 1.5.

36. The thromboplastin reagent of claim 29, having a prothrombin time ratio for 1% Factor VII of at most 1.2.

37. The thromboplastin reagent of claim 29, having a prothrombin time ratio for 1% Factor II of at least 2.

38. The thromboplastin reagent of claim 29, having a prothrombin time ratio for 1% Factor II of at least 5.

39. The thromboplastin reagent of claim 29, wherein the Tissue-factor is r-tissue-factor.

40. The thromboplastin reagent of claim 29, wherein the Factor-seven is human Factor VIIa.

41. The thromboplastin reagent of claim 29, wherein the Factor-seven is present in an amount of at least 150 pM Factor VIIa equivalents.

42. The thromboplastin reagent of claim 29, wherein the Factor-seven is present in an amount of at least 200 pM Factor VIIa equivalents.

43. A method of administering an anticoagulant drug, comprising:
administering an anticoagulant drug to a patient in need thereof; and
measuring the time to clot formation of the patient's plasma mixed with the thromboplastin reagent of claim 29.

44. A thromboplastin reagent, comprising:
(a) r-tissue-factor,
(b) at least 150 pM Factor VIIa,
(c) phosphatidylcholine,
(d) phosphatidylserine, and
(e) $Ca^{2+}$,
wherein the thromboplastin reagent has an International Sensitivity Index of at most 1.5, a prothrombin time ratio for 1% Factor VII of at most 1.5, and a prothrombin time ratio for 1% Factor II of at least 2, and
the thromboplastin reagent is in dried form.

45. The thromboplastin reagent of claim 44, further comprising at least one alkali metal salt.

46. The thromboplastin reagent of claim 44, having an International Sensitivity Index of at most 1.2.

47. The thromboplastin reagent of claim 44, having an International Sensitivity Index of 0.8 to 1.5.

48. The thromboplastin reagent of claim 44, having a prothrombin time ratio for 1% Factor VII of at most 1.2.

49. The thromboplastin reagent of claim 44, having a prothrombin time ratio for 1% Factor II of at least 5.

50. The thromboplastin reagent of claim 44, wherein the Factor VIIa is human Factor VIIa.

51. The thromboplastin reagent of claim 44, wherein the Factor VIIa is present in an amount of at least 200 pM.

52. The thromboplastin reagent of claim 44, having a prothrombin time ratio for 1% Factor VII of at most 1.2, and a prothrombin time ratio for 1% Factor II of at least 5,
wherein the Factor VIIa is human Factor VIIa, and
the Factor VIIa is present in an amount of at least 200 pM.

53. A method of administering an anticoagulant drug, comprising:
administering an anticoagulant drug to a patient in need thereof; and measuring the time to clot formation of the patient's plasma mixed with the thromboplastin reagent of claim 43.

54. A method of making a thromboplastin reagent, comprising:
adding Factor-seven to a synthetic thromboplastin reagent comprising Tissue-factor; and
drying the thromboplastin reagent.

55. The method of claim 54, wherein the dried thromboplastin reagent has an International Sensitivity Index of at most 1.5.

56. The method of claim 54, wherein the dried thromboplastin reagent has an International Sensitivity Index of 0.8 to 1.5.

57. The method of claim 54, wherein the dried thromboplastin reagent has a prothrombin time ratio for 1% Factor VII of at most 1.5.

58. The method of claim 54, wherein the dried thromboplastin reagent has a prothrombin time ratio for 1% Factor VII of at most 1.2.

59. The method of claim 54, wherein the dried thromboplastin reagent has a prothrombin time ratio for 1% Factor II of at least 2.

60. The method of claim 54, wherein the dried thromboplastin reagent has a prothrombin time ratio for 1% Factor II of at least 5.

61. The method of claim 54, wherein Tissue-factor present in the thromboplastin reagent is r-tissue-factor.

62. The method of claim 54, wherein the Factor-seven is human Factor VIIa.

63. The method of claim 54, wherein the Factor-seven is added in an amount of at least 150 pM Factor VIIa equivalents.

64. The method of claim 54, wherein the Factor-seven is added in an amount of at least 200 pM Factor VIIa equivalents.

* * * * *

UNITED STATES PATENT AND TRADEMARK OFFICE
CERTIFICATE OF CORRECTION

PATENT NO.         : 7,148,067 B2
APPLICATION NO. : 10/931282
DATED                  : December 12, 2006
INVENTOR(S)       : James H. Morrissey and Stephanie A. Smith It is certified that error appears in the above-identified patent and that said Letters Patent is hereby corrected as shown below:

On the Title Page, Item (56)
In Other Publications

Line 13, please delete "Dieto" and insert --Diego--.

Page 2, line 35, please delete "purificationof" and insert --purification of--.
Page 2, line 39, please delete "ationof" and insert --ation of--.
Page 2, line 52, please delete "ration" and insert --ratio--.
Page 2, line 59, please delete "ration" and insert --ratio--.
Page 2, line 3, please delete "U(" and insert --U)--.
Page 2, line 13, please delete "Vhem" and insert --Chem--.
Page 2, please delete lines 20-22 and insert --lipids"., Biochim. Biophys. Acta, vol. 1567, pp. 204-212, (2002).--
Page 3, line 29, please delete "3551" and insert --351--.
Page 3, line 3, please delete "pp. 267".
Page 3, line 33, please delete "VIII" and insert --VII--.
Page 3, line 36, please delete "FVCIIa" and insert --FVIIa--.
Page 3, line 71, please delete "glycosylationof" and insert --glycosylation of--.

Col. 17, line 56, please "1-1 000" and insert --1-1000--.
Col, 17, line 60, please insert a comma after "reagent".
Col. 19, line 3, please delete "43" and insert --44--.

Signed and Sealed this

Thirteenth Day of November, 2007

JON W. DUDAS
*Director of the United States Patent and Trademark Office*